United States Patent [19]
Durzan et al.

[11] Patent Number: 5,821,126
[45] Date of Patent: Oct. 13, 1998

[54] METHOD FOR CLONAL PROPAGATION OF GYMNOSPERMS BY SOMATIC POLYEMBRYOGENESIS

[75] Inventors: Don J. Durzan, Davis, Calif.; Pramod K. Gupta, Federal Way, Wash.

[73] Assignee: The Regents of the University of California, Oakland, Calif.

[21] Appl. No.: 398,060

[22] Filed: Mar. 3, 1995

Related U.S. Application Data

[63] Continuation-in-part of Ser. No. 908,958, Jul. 6, 1992, abandoned, and Ser. No. 876,695, Apr. 28, 1992, abandoned, which is a continuation of Ser. No. 701,597, May 13, 1991, abandoned, which is a continuation of Ser. No. 537,863, Jun. 12, 1990, abandoned, which is a continuation of Ser. No. 65,610, Jun. 22, 1987, abandoned, which is a continuation-in-part of Ser. No. 932,719, Nov. 19, 1986, abandoned, said Ser. No. 908,958, is a continuation of Ser. No. 436,095, Nov. 13, 1989, abandoned, said Ser. No. 932,719.

[51] Int. Cl.$^6$ .................. A01H 4/00; A01C 1/06

[52] U.S. Cl. .................. 435/422; 435/420; 435/430; 435/430.1; 435/431; 47/57.6; 47/58

[58] Field of Search .................. 435/240.45, 240.48, 435/240.49, 240.54, 240.46, 420, 422, 430, 430.1, 431; 800/DIG. 49–51; 47/57.6, 58

[56] References Cited

PUBLICATIONS

Hakman et al. 1985. Plant Science 38:53–59.
Hakman et al. 1985. J. Plant Physiol. 121(2):149–158.
Krogstrup, P. 1986. Can. J. For. Res. 16:664–668.
Gupta et al. 1987. Bio/ Technology 5(2):147–151.

*Primary Examiner*—David T. Fox
*Attorney, Agent, or Firm*—Hana Verny

[57] ABSTRACT

A method for clonal propagation by somatic polyembryogenesis. The method allows for clonal propagation of embryonal suspensor mass resulting in true-to-type suspensor development of the conifer embryo leading to development of plantlets and plants.

28 Claims, 8 Drawing Sheets

METHOD FOR CLONAL PROPAGATION OF GYMNOSPERMS BY SOMATIC POLYEMBRYOGENESIS

This application is a continuation-in-part of U.S. Ser. No. 07/908,958 filed on Jul. 6, 1992, now abandoned, which is a continuation of U.S. application Ser. No. 07/436,095, filed on Nov. 13, 1989, now abandoned, which is a continuation of U.S. Ser. No. 06/932,719 filed on Nov. 19, 1986 now abandoned. This application is also a continuation-in-part of U.S. application Ser. No. 07/876,695, filed on Apr. 28, 1992, now abandoned, which is a continuation of U.S. Ser. No. 07/701,597, filed on May 13, 1991, now abandoned, which is a continuation of U.S. Ser. No. 07/537,863 filed on Jun. 12, 1990, now abandoned, which is a continuation of 07/065,610 filed on Jun. 22, 1987, now abandoned, which is a continuation-in-part of U.S. Ser. No. 06/932,719 filed on Nov. 19, 1986, now abandoned.

This invention was made with government support under Grant Nos. PSW83-0038 CA and 84-0011 CA with the United States Department of Agriculture and the University of California. The government has certain rights in this invention.

BACKGROUND OF THE INVENTION

1. Field of the Invention

The current invention concerns a method for clonal propagation of gymnosperms by somatic polyembryogenesis. In particular, the invention concerns a method for production of embryonal suspensor mass able to develop into a generation of gymnosperm clonal somatic plant proembryos. The method allows clonal propagation of somatic cells resulting in true-to-type development of the conifer embryo leading to development of plantlets and plants. Additionally, the invention concerns cloning gymnosperm embryos, propagating plantlets, trees, encapsulating embryos, storing embryos over a long period of time and diagnosing the developmental stages and condition of plant cells by staining and microscopy.

2. Background Art and Related Art Disclosures

Somatic polyembryogenesis for clonal propagation of gymnosperm, if achieved, would have far reaching effect on clonal forestry and agriculture development.

If successful, somatic polyembryogenesis (SPE) would allow propagation of seeds obtained from a selected cross of elite parents especially in advanced breeding programs where the progeny are expected to be superior to the average of the population. The selection and rescue of viable embryonal suspensor masses or of explants from elite tree minimizes the introduction of undesirable traits introduced by introgression of foreign pollen or mutations that occur in sexual reproduction.

Additionally, SPE would allow the controlled maintenance and multiplications on demand of the genotype by cell and tissue culture technology. This would remove the constraints to tree production where seed production varies year to year with some years giving no seed at all. The controlled culture of cells and mass production of embryos would further enable convenient manipulation (genetic and non-genetic) of the genotype under laboratory rather than field conditions. Moreover, through modifications of the medium and the provision of reliable food supply to the embryos, more uniform and robust embryos can be recovered, preconditions for field plantings in genotype and environment tests. Normally in nonsomatic polyembryogenesis only one embryo is obtained from one seed. SPE would enable many copies of the embryo to be cloned and this would enable a wider testing of genotype performance over a wider range of environments. This cannot be done with one embryo from one seed.

While previously simple somatic polyembryogenesis from callus of mature Sugar pine embryos was described (*Biotechnology*, 4:643 (1986), a true-to-conifer-type somatic polyembryogenesis that proceeds from a proliferating embryonal suspensor cell mass was not reported before this invention was developed.

Previous attempts to provide true-to-type somatic polyembryogenetic clonal propagation were not successful. These previous attempts for clonal propagation with somatic cells did not produce and did not report embryonal suspensor mass development or true-to-type and sequential development characteristics of the conifer embryo leading to plantlets able to grow in soil.

The earliest attempts to achieve somatic embryogenesis in gymnosperms were described in *Canadian Department of Forestry and Rural Development, Res. Rpts.*, 24:30 (1970)., *Abstr. Comm. Inst. For. Fenn.*, 75:16 (1971); *Proc. 50th Ann. Conf. Appleton*, Wis., May 8–10, pp. 36–60 (1978), *Proc. V. Intl. Congr. Plant Cell and Tissue Culture*, July 11–16, Tokyo, Japan, pp. 113–114 (1982); and U.S. Pat. No. 4,217,730. Although these attempts were made since around 1970, none of these publications reported clonal somatic or gametophytic polyembryogenesis or true-to-conifer-type embryonic development.

The earlier publications reported appearance of embryo and suspensor-like structures in cell suspensions of embryonic tissues of white spruce and jack pine in undefined media, *Res. Rpts.* (1970) supra *Plant Sci. Lett.*, 38:53–59 (1985) reported somatic embryogenesis in a Norway spruce "callus" using tissue from immature seeds and *Can. J. Forestry Res.*, 15:1088–1091 (1985) reported the same in Larch. None of these others, however, discovered the cellular origin of the process for production of or achieved true-to-type clonal somatic or gametophytic polyembryos, nor did they recognize or achieve the specific attributes of cleavage polyembryony and the polyembryonic multiplication process as described herein. Also, none of the reported research generated somatic embryos in any significant number.

Similarly, none of the publication disclosed diagnostic tests which could distinguish the developmental stages of plant embryogenesis. As a diagnostic tool, *Biotech.*, 4:763 (1984) reported diagnostic color test for somatic embryogenesis in Prunus in cell suspensions. *Chromosome Techniques. Theory and Practice*, Frakenham Press, Ltd., Norfolk, page 121, (1980), and *J. Exp. Bot.*, 22:756–758 (1971) described staining methods for examining cells. However, none of these articles utilized the use of chromatin or glycoprotein and viability test stains for determining the free nuclear and early developmental stages of plant embryogenesis.

One of the many difficulties in propagating species of gymnosperm plants has been a lack of preservation techniques which would preserve the embryos in a viable state even after a long term storage. While U.S. Pat. No. 4,562,663 disclosed a method for encapsulating embryos and *Can. J. For. Res.*, 14:750–753 (1984) described a method for long-term storage of angiosperm callus, none of these publication have, however, described the long-term storage of gymnosperm embryos or plant tissue which would assure that such embryos would be viable following the long-term storage. Such long-term storage would be important for purposes of testing the embryo's genotype, stock build-up, recycling, quality control and testing of plantlets.

It is therefore a primary object of the current invention to provide a method for plant somatic polyembryogenesis, the cleavage of the polyembryonic masses, maturation of the plant embryos, generation of plants from embryos, encapsulation of the plant embryos in alginate gels for storage, conversion of these stored embryos into plantlets, a diagnostic staining techniques for determining the development stages of plant embryogenesis and viability of cloned somatic embryos, and a long-term storage of the embryos for later use and recovery of the viable embryos following the storage for field tests and mass production.

All patents, patent applications and publications cited herein are hereby incorporated by reference.

SUMMARY OF THE INVENTION

One aspect of the current invention is a process for propagating new trees, comprising methods for cloning gymnosperm embryos, encapsulating embryos, storing embryos over a long period of time and diagnosing the development and condition of plant cells by staining and microscopy.

Another aspect of the current invention is a method for clonal generation of gymnosperm somatic plant proembryos, comprising culturing cells from mature elite trees such as nucellar tissues, young leaves, rejuvenated tissues, or from individual rescued embryos from immature or mature seeds from controlled or natural crosses between mature trees wherein such culturing comprises the aseptic incubation of rescued cells and explants on a semi-solid culture medium or in cell suspension cultures.

Another aspect of the current invention is a method for repetitive regeneration of gymnosperm somatic proembryos, comprising repetitive subculturing of an embryonal-suspensor mass in a prescribed plant basal medium.

Still another aspect of the current invention is a method for generating gymnosperm clonal plant somatic embryos, comprising obtaining an excised zygotic embryo from a seed or a protodermal cellular explant, incubating the explant in darkness or in a weak diffuse light on a first plant basal medium containing promotory growth regulators until an embryonal-suspensor mass develops, transferring the embryonal-suspensor mass into a second basal medium containing a second concentration of plant growth regulators, maintaining embryonal-suspensor mass in darkness or weak diffuse light until proembryos develop, transferring the embryonal-suspensor mass containing developed proembryos into a third basal medium containing a growth regulator concentration effective for the development of globular embryos, culturing the embryonal-suspensor mass in darkness or weak diffuse light until globular embryos develop, transferring the globular embryos into a forth basal medium containing no growth regulator and incubating the embryos in light until elongated somatic embryos develop.

Still yet another aspect of the current invention is a method for generating gymnosperm clonal plantlets, comprising a series of manipulations identical to the series of manipulations required for the production of somatic plant embryos with the addition of transferring somatic embryos into a fifth basal medium containing activated charcoal and cyclitol without the presence of organic nitrogen and plant growth regulators, and incubating those somatic embryos until plantlets develop.

Still another aspect of the current invention is a method for storing the embryos and proembryos and maintaining their viability during storage, comprising encapsulating the embryos, proembryos and embryonal-suspensor mass in an alginate gel and storing the encapsulated proembryos and embryos at temperature not above 1°–4° C., or in liquid nitrogen in the dark.

Still yet another aspect of the current invention is a method for inhibiting continued polyembryogenesis and increasing the yield of somatic embryos, comprising addition of abscisic acid to the medium.

The final aspect of the current invention are diagnostic methods for determining the development stages of plant embryogenesis and organogenesis comprising observing the plant cells by light or fluorescence microscopy and staining the plant cells with chromatin or glycoprotein stains and/or viability test stains and observing the cells by microscopy to ensure that the normal sequence of development steps will occur.

DEFINITIONS

As used herein:

"2,4-D" means 2,4-dichlorophenoxyacetic acid.

"ABA" means abscisic acid.

"Auxins" means natural and synthetic plant growth regulators that promote cell elongation and the establishment of physiological states that promote embryogenesis. Examples of auxins are napthalene-2-acetic acid, 2, 4-D dichlorophenoxyacetic acids, β-indole acetic acid, 2-benzothiazole acetic acid, parachlorophenoxyacetic acid and picloram.

"BA" or "BAP" means $N^6$-benzylaminopurine and is also known as $N^6$-benzyladenine.

"BM" means basal medium.

"Callus" means a growth of unorganized, unconnected or loosely connected plant cells normally produced from culturing of an explant.

"Cell and tissue culture" means the process by which cells or tissue excised from a donor plant is nourished and conditioned under aseptic conditions on a series of culture media to establish cultures for maintenance or for production of multiple plantlets genetically identical to the donor and in some cases plantlets with aberrant phenotypes, also called somaclonal variants.

"Cell suspensions" means the suspension of cells in a mechanically agitated liquid nutrient or basal medium. Agitation provides aeration and the establishment of cells in liquid nutrient enables hydrodynamic processing of the developing cells. The cell suspension stage is shown in FIG. 1, Step 6.

"CH" means casein hydrolysate.

"Cleavage polyembryogenesis" means the reconstitution of multiple new embryos from a single embryo by a process that cleaves the single embryo into multiple embryos. This occurs spontaneously in some seeds in nature. Cleavage process is enhanced in suspension culture especially in genotypes that do not show cleavage in nature. For example, Norway spruce is not normally considered a cleavage polyembryonic species but when rescued and cultured, the individual embryos will cleave. The cleaving mass of embryos comprises the embryonal-suspensor mass that occurs naturally in immature seed and is rescued for culture purposes. If cleavage of individual embryos does not occur naturally, the cleavage process is expressed under culture conditions and is distinguished by microscopic examination or by the visual observation that multiple embryos develop spontaneously from a single embryo. The resultant multiple embryos that are reconstituted are monozygotic in origin. This is distinct from simple polyembryony where each embryo arises from a different egg and the resultant multiplicity of embryos represents fraternal genotypes because of multiple fertilizations.

"Cleavage polyembryony" means that more than one embryo results by mitotic division (during each cleavage) of the zygote into two or more units, each developing into an embryo. Cleavage polyembryony is monozygotic in that single zygote produces multiple embryos by cleavage. The resultant embryos are monozygotic in origin and genetically identical and represent the new generation.

"Conifers" means a botanical order (Coniferales) that represents most evergreen trees and shrubs growing cones.

"Conifer-type" means one of the four types of proembryo development in conifers. This type of proembryogeny occurs in conifers and taxads and represents a basal plan for embryonic development. The terminology of conifer-type development is presented by Singh, *Embryology of Gymnosperms*, Encyclopedia of Plant Anatomy, Gebruder, Borntraeger, Berlin, (1978). The terminology is used in describing stages in the process.

"Conversion" means the equivalent of the germination of a seed but refers to embryos that have been grown from somatic cells by the process of cleavage somatic polyembryogenesis.

"Cytokinins" means natural and synthetic plant growth regulators that affect the organization of developing tissues and affect cells mainly by cell division. Through cell division, the developmental information in mother cells is transferred to daughter cells in the embryogenesis. Examples of cytokinins are kinetin and $N^6$ benzyladenine or $N^6$-benzylaminopurine.

"Embryogenic callus" means callus that has the potential to produce embryos. Embryogenic callus contains daughter cells that divide and grow in a random fashion. These cells are not normally embryogenic unless the capacity for embryogenesis is somehow induced in each cell. Since callus is usually produced by an overexposure to synthetic plant growth regulators, genetic aberrations are common. This means that embryos that come from each induced callus cell may represent a genotype different from the tissues explanted to start the callus. When these embryos emerge in a callus, the mass of cells is called an embryogenic callus. Callus is non-embryogenic when upon culturing only more callus tissue develops but no embryos. For these reasons, and because of the absence of a callus phase in somatic polyembryogenesis (SPE), the new term somatic polyembryogenesis is used to distinguish the origins of embryos derived from a callus. It is also important to recognize that the multiple embryos in SPE multiply by a natural cleavage step and new embryo does not need to be induced from a callus cell by introducing a specific step or process.

"Embryogenesis" means the process of developing natural or somatic embryos.

"Embryogenic cell suspension" means a cell suspension derived from any source that contains embryogenic cells. In this invention, a specific diagnosable and recognizable source is used and all callus phases are physically removed to enable embryogenesis. The result is that this process, cleavage multiplication of embryos occurs spontaneously in a way as it occurs in nature where callus is not present.

"Embryonal-suspensor mass" or "ESM" means the explant or rescued mature or immature embryo and its associated suspensor cells from the developing seed just after fertilization. ESM is distinct from embryogenic callus. The callus consists of random and nondescript populations of cells which do not yield true-to-conifer type somatic polyembryogenesis. ESM is not a callus because daughter cells in the ESM repetitively yield somatic embryos and a cleavage polyembryogenic process. ESM is characterized as a white, slimy, proliferating totipotent mass of cells emerging from any of the developmental stages of the rescued zygotic embryo or from protodermal cells or tissues of the mature mother tree that have been induced to become embryogenic either as a callus or without a callus stage. The ESM has distinct cytochemical features that distinguishes it from a callus so that callus can be removed physically from the cultures during subculture.

"Explant" means a piece of tissue taken from the donor plant for culturing under aseptic conditions.

"GLN" or "gln" means L-glutamine.

"IAA" means β-indoleacetic acid.

"KN" means kinetin.

"Meristematic tissue" means tissue comprising and originating from the root and shoot meristem of at least partially developed plant. Meristematic tissue does not include plant cells appearing before organ formation as in zygotic or somatic proembryos and embryos which contain promeristematic tissue.

"Morphogenic" means capable of organized growth in the sequence found in true-to-type plants.

"MS" means Murashige-Skoog medium.

"NNA" means naphthalene-2-acetic acid.

"Nucellar" means tissues that represent the genotype of the mature mother tree and contribute to ovule development. Embryos developing from this tissue are sometimes referred to as sporophytic and the process is called false polyembryony. Nucellar polyembryony occurs for example in Citrus species.

"Parthenocarpic" means the development of a seedless fruit or seed which lacks embryos. These processes are distinct and separate from the process of cleavage polyembrogenesis.

"Plantlet" means a conifer that is asexually reproduced by tissue culture.

"Proembryogeny" means the preliminary stage of development of the embryo. Proembryogeny is recognized by proembryonal stages that usually comprise a free-nuclear stage followed by cellularization into a proembryo without its suspensor system. The proembryogeny stage is shown in FIG. 1, stage 8. Proembryogeny is distinct from both the early embryogeny globular embryo development and from the late embryogeny, which represents establishment of the polar meristems, that is roots and shoots and the subsequent development of the embryo into plantlets and plants.

"Polyembryogenesis" means the production of more than one embryo from a single cell or embryo.

"Polyembryony" means a generic process referring to the production of multiple embryos. The source of the multiple embryos however must be specified as simple, cleavage, sporophytic, etc., to further define how this process originates and differs from other similar processes.

"Proliferating embryonal suspensor mass" means very rapid growth of ESM. The cleavage and developmental process is more rapid than in a callus which is also a rapid growth stage. Proliferation refers not only to the rapid growth rate of the ESM but also to the rapid multiplication by cleavage of individual embryos in the ESM.

"Promeristematic" means early embryonal and proembryonal plant cells that produce meristems.

"Repetitive conifer-type somatic embryos" means embryos derived from a zygotic polyembryogenic process based on true-to-type developmental expressions of cells in the zygotic embryo but used in reference to the multiplications of cleaving somatic embryos from the embryonal-suspensor mass.

"PGR" means promotory growth regulators, such as cytokinins, 2,4-D, NAA, IAA, auxins, BA, BAP, abscisic acid, thidiazuron and kinetin.

"Protodermal" means cells or tissue giving rise to the cellular surface of a plant.

"Protoplast" means a plant cell without the cell wall.

"Simple polyembryogenesis" means and occurs when several egg cells develop and each is fertilized by a separate sperm. Simple polyembryogenesis is different from somatic polyembryogenesis where multiple clonal embryos develop from a single fertilized egg, for example, the process is monozygotic. Simple polyembryogenesis is polyzygotic in that the fertilization of multiple egg produces multiple zygotes.

"Somatic embryo" means derived from the non-reproductive cells.

"Somatic proembryo" means an asexually produced prospective embryonic plantlet at an early stage of proembryonal development with cells that are differentiated in embryonic potential. At this stage, the suspensor of the axial tier has not yet formed.

"Somatic polyembryogenesis" or (SPE) means a process whereby multiple embryos are mass produced from an embryonal suspensor mass by a cleavage polyembryonic step. The origin of the multiple embryos is somatic as opposed to being derived directly from a reproductive cell such as a gamete, egg, or sperm.

"Sphaeroblast" is a globular cellular mass of cells resembling a proembryo but derived from callus. Sphaeroblast growth is distinguished by the internal production of precociously vascularized cells. Sphaeroblasts can polarize and resemble the early stage of embryonic development, however, they do not produce synchronized root and shoot development as in true-to-type zygotic or somatic polyembryogenesis. Sphaeroblasts are often confused with somatic embryos because of the similarity in outward appearance.

"Sporophytic polyembryony" means that adventitious embryos arise by sporophytic budding from the nucellus and from the integument in flowering plants. The embryos are usually identical to each other and to the mother plant.

"Suspensor" or "suspensor cells" means a group or chain of cells that is produced at one end of the developing proembryo which usually serves to put the embryo into contact with food supply for nourishment.

"Totipotent" means capable to generate or regenerate a whole organisms. Totipotency in plant cells means that they are fully recapitulating all of the growth and developmental stages found in the life cycle as occurs in nature.

"True-to-type" means that the genotype is an exact copy according to the model reference for that genotype.

"True-to-type developmental stages" means according to genotypic developmental plan.

BRIEF DESCRIPTION OF DRAWINGS

The file of this patent contains at least one drawing executed in color. Copies of this patent with color drawing (s) will be provided by the Patent and Trademark Office upon request and payment of necessary fee.

DETAILED DESCRIPTION OF THE INVENTION

Figure 1:
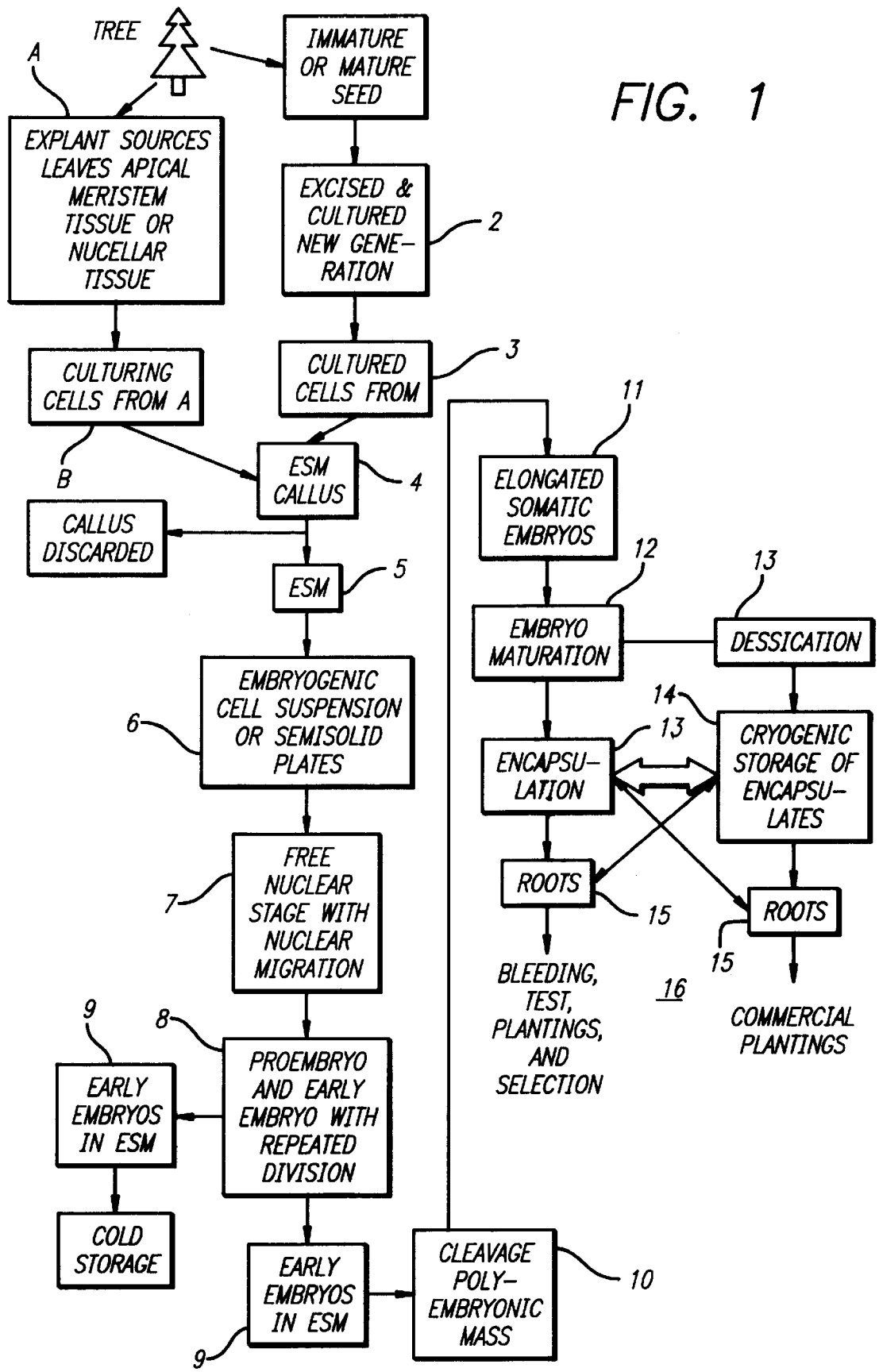
FIG. 1 is a schematic illustration of the process for somatic polyembryogenesis and plantlet generation.

In accordance with the present invention, methods are provided for obtaining and cloning gymnosperm embryos, propagating new plantlets, plants and trees, encapsulating embryos, storing embryos over a long period of time and diagnosing the development and condition of plant cells by staining and microscopy.

The current invention provides a method for generating gymnosperm clonal plant somatic embryos, comprising obtaining an excised zygotic embryo from a seed or a protodermal cellular explant, incubating the explant in darkness or in a weak diffuse light on a first plant basal medium containing promotory growth regulators until an embryonal-suspensor mass develops, transferring the embryonal-suspensor mass into a second basal medium containing a second concentration of plant growth regulators, maintaining embryonal-suspensor mass in darkness or weak diffuse light until proembryos develop, transferring the embryonal-suspensor mass containing developed proembryos into a third basal medium containing a growth regulator concentration effective for the development of globular embryos, culturing the embryonal-suspensor mass in darkness or weak diffuse light until globular embryos develop, transferring the globular embryos into a forth basal medium containing no growth regulator and incubating the embryos in light until elongated somatic embryos develop.

The method for generation of proembryos, embryos, plantlets and plants according to the invention includes the clonal propagation of various gymnosperm species from embryonal-suspensor masses (ESMs) by somatic polyembryogenesis. The method provides conditions for production of embryonal suspensor mass able to develop into a generation of gymnosperm clonal somatic plant proembryos and allows clonal propagation of somatic cells resulting in true-to-type development of the conifer embryos leading to development of plantlets and plants.

The invention encompasses a process for the production of somatic embryos that are "conifer-type" in basal plan of development through the use of cell and tissue culture using liquid medium suspensions. The basal plan of "conifer-type" processes for true-to-type embryogeny is important for the repetitive clonal origins of embryos from ESM by the cleavage origin and multiplication of embryos by a repetitive process that is developmentally true-to-type for the selected conifer genotype. The process enables mass production of clonal embryos, plantlets and plant from unmodified mature or immature seeds.

The SPE process differs from simple polyembryogenesis known previously or from somatic embryogenesis where nucellar tissues are employed and where somatic cells or tissues, often derived from a callus, are employed and where the embryos may be variant due to aberrations in a callus stage or due to advanced differentiation of the starting cells or due to incomplete dedifferentiation of the starting cells. This process also differs from sporophytic polyembryony where the nucellus is the starting material and where the progeny represents the mother tree. However, nucellar tissues may be selected and induced to recapitulate somatic polyembryogenesis where the progeny arise by cleavage of a single embryo induced in the explanted nucellar tissues.

The early literature on cell and tissue culture does not distinguish among an embryonic callus, simple polyembryogenesis, cleavage, polyembryogenesis, or sporophytic polyembryogenesis. However, clearly it was not evident that somatic polyembryogenesis was possible with a rescued or induced embryonal suspensor mass until the diagnostic studies according to the invention were performed. The invention discovered two important attributes which occur with somatic polyembryogenesis but do not occur with somatic embryogenesis or other nonsomatic polyembryogenesis. First, embryogenic and polyembryogenic cells are cytochemically distinguished as already embryonic from the start by staining and microscopic techniques described in the application. There is no need to induce embryogenesis or the cleavage process. Second, all of the embryonal cells derived through somatic polyembryogenesis are of the same genotype, that is true-to-type next generation. SPE represents the potential of the new generation. Somatic polyembryogenesis (SPE) according to the invention is a spontaneous and repetitive process that can be maintained and enhanced with plant growth regulators such as auxins and cytokinins on specially formulated and supplemented media. SPE according to the invention is particularly useful for clonal propagation of gymnosperm embryos, specifically for the reproduction of Pinaceae species. Somatic polyembryogenesis has been successfully achieved in Douglas-fir, Sugar pine, Loblolly pine and Norway spruce.

Applied multiple diagnostic tests at strategic development stages improve selectivity and efficiency of the SPE process, storage and conversion of embryos. Storing of somatic polyembryos at low temperatures using an artificial coat encapsulation is designed for low temperature storage and to facilitate machine handling.

The present invention provides the capability for greatly increasing the stock of gymnosperm species and controlling the genotype by means of cellular tissue culture and is useful for mass production of plantlets for afforestation, reforestation and for ornamental commercial use.

I. Method for Somatic Polyembryogenesis for Clonal Propagation of Gymnosperms

A method for somatic polyembryogenesis for clonal propagation generally consists of 16 steps illustrated in FIG. 1. Each step is seen as a box.

Step 1 concerns selection of genetic material for clonal propagation by somatic polyembryogenesis. Cones, seeds, shoots or roots for clonal propagation of selected tree genotype are identified and isolated.

Step 1 involves obtaining a zygotic embryo from cones, seeds, shoots or roots (Step 1) or explants such as the protodermal cells, leaves, apical meristem tissue or nucellar tissue (Step A) by removing mature or immature seeds or explants from a female cone collected after approximately one to seven weeks, preferably four to five weeks, following fertilization. Explants can also be taken from leaves, apical meristems or nucellar tissues from mature trees or from rejuvenated clones or trees that have not yet reached the reproductive state (Step A). Then, the seeds, cones, shoots, roots or explants are surface sterilized, typically by treating them with 0.01–1%, preferably 0.1% (w/v) of detergent, preferably Linbro detergent, Tide or Tween obtained from Fisher Scientific, for 3–10, preferably 5 minutes, and washing them three to four times with distilled water.

In alternative, the seeds, cones, shoots, roots or explants are treated with 30% peroxide (v/v) for ten minutes, washed several times with distilled water, or sterilized with 0.1%–1%, preferably 0.1% (w/v), $HgCl_2$ for ten minutes, and washing them eight to ten times in sterile water while maintaining aseptic conditions.

Step 2 concerns isolation and rescue of sterilized seeds, cones, roots, shoots or explants obtained in Step 1 or Step A and culturing these tissues on any appropriate culture medium, typically MS-2 or DCR-2, any appropriate basal culture medium (such as MS or DCR) enriched to bring out hidden contamination in the cells or explant. After the asepsis of the culture is ensured a basal medium enriched with plant growth regulators at a level compatible with the selected explant and genotype is used for Step 3 and Step B to initiate formation of an ESM from Step A and Step B or further development of the existing and rescued ESM from seeds (Steps 1–3). The recovered ESMs are represented in Step 4.

Rescue of the ESM is achieved by excising ovules with female gametophytes separating an embryonal suspensor mass with its immature embryo(s) attached to a suspensor mass and immature embryos attached to a fragment of the gametophyte, or mature embryos with suspensor mass, by removing the seed with its attached residual suspensor mass (if available), by removing the coat, and dissecting out female gametophytes with proembryo, embryo and suspensor.

Step 2 includes proliferation of ESM by subculturing it in a cell suspension by incubating the EMS in MS-2 or DCR-2 medium as described in Examples 1–5 and also according to method described in *Plant Cell Repts.*, 4:177 (1985) and further incubating the culture in dark at about 21°–25° C., preferably at 23° C., for 3 to 8, preferably 5 to 6 weeks to obtain cultured cells. Resulting cultured cells, seen in Step 3 contain the ESM and possibly callus.

Step 4 onwards concerns the culturing and development of the ESM by subculturing it in a cell suspension or on a semi-solid plate.

The processes following step 4 (box 4) involve the culturing and selectively, by removing callus, propagating a new generation from EMS.

The medium at Step 4 is preferably MS-1 or DCR-1 medium containing promotory growth regulators (PGR), such as 2,4-D, kinetin and BAP. The concentration of these PGRs differ depending on the plant species, but are typically from 30–60 mM, preferably about 50 $\mu$M for 2,4-D and 10–30 $\mu$M, preferably about 20 $\mu$M for BAP and kinetin for MS-1 or DCR-1 medium.

The length of the incubation differs, depending on the plant species. Typically, it is from 1 to 8 weeks, preferably from 4–5 weeks for Douglas Fir and Sugar Pine and 3–4 weeks for Loblolly pine, for example. Other species may optimally develop ESM in shorter or longer period of time. The incubation is typically in darkness and at 21° C.–25° C., preferably at about 23° C.

After one to six weeks of culturing on the media to recover the ESM, a white mucilaginous translucent slimy ESM develops around the female gametophyte typically from 5%–25% of the immature seeds. ESM is characterized as a white, proliferating totipotent mass of cells emerging from the zygotic proembryo or protodermal cells of shoots and roots. ESM is distinct from nonembryogenic callus.

ESM and callus are identified by diagnostic tests, separated and callus is discarded. Diagnostic techniques are described in detail below. Briefly, nonembryogenic and embryogenic cells are distinguished by the double diagnostic staining techniques. Both the nucleus and cytoplasm of embryonal cells stains red with acetocarmine. Nonmorphogenic cells do not stain with acetocarmine. For nonmorphogenic cells, only the nucleus stains weakly with acetocarmine. Callus, suspensors and nonembryogenic cell stain blue with Evan's blue but callus does not have suspensor cells attached to the early embryos.

ESM types are selected by light microscopic inspection and by single or by double-staining methods for evidence of "conifer-type" somatic polyembryogenesis. The preferred mode is to first stain the cells with a chromatin (acetocarmine) or glycoprotein/DNA (Feulgen) stain and then with a viability (Evan's blue) test stain. The preferred chromatin or glycoprotein stains are acetocarmine or Feulgen but others such as Orcin may be used. The preferred viability test stain is Evan's blue but others, such as neutral red, fluorescein diacetate and Janis green B can be advantageously used. Prospective somatic proembryos arise as a "basal plan" from primary embryonal cells in the ESM.

Cells derived from friable and non-friable embryonic callus under identical culture conditions are distinctively different in shape and growth pattern in that they do not incorporate acetocarmine or exhibit the red stain resulting from absorption of acetocarmine characteristics of the proliferating embryonal-suspensor mass cells. The above diagnostic identifications of callus and ESM are involved in steps 4 and 5 in FIG. 1.

Tissues or cells staining red with acetocarmine which are identified as embryogenic are separated and moved to Step 5. Callus represented in the box called "callus discarded" is removed from ESM culture and discarded.

Steps 6, 7 and 8 involve culturing the cells, proembryo, embryo and suspensor from Step 5 on induction MS or DCR medium.

Step 6 concerns subculturing of ESM in cell subculture to induce the development of proembryo and early embryo.

Step 6 involves proliferation of the ESM in darkness with or without zygotic embryos by subculturing ESM on agar every nine to ten days in a cell suspension. For this purpose, ESM is transferred to the liquid culture medium, preferably into modified MS or DCR, such as MS-2 or DCR-2, to establish cell suspension cultures. Inoculation density is adjusted to be about 10 grams fresh weight per 100 ml of culture medium in a flask shaken for aeration at rate from 1–50 rpm in Erlenmeyer flasks or 1 rpm in nippled flasks.

Suspensions are maintained by subculturing every 5–12 days, preferably every 7 days on fresh medium for 3–4 weeks. The cells can be maintained indefinitely by this step. The cells have been kept on semi-solid plates or in suspension cultures for nearly 7 years as a stock for use in recovering plants.

Steps 7 and 8 aim to enhance the development and multiplication of proembryos and early embryos in the ESM either as a suspension or on a semi-solid medium.

Step 7 concerns the recovery of new embryos starting with a single cells stage and with cells having the characteristic development of a free-nuclear proembryo.

Proembryonal cells developed from the migration of nuclei in Step 7 are maintained by mitosis in culture medium preferably MS-3 or DCR-3 containing 2,4-D. If needed, the progress through the free-nuclear stages can be followed by removing cell samples from the culture medium and staining them with acetocarmine or Feulgen and Evan's blue. Nuclei that contribute to the formation of the proembryo staining are identified by red staining with acetocarmine and Feulgen reaction. Other nuclei which stain more intensely blue with Evan's blue contribute to the formation of the suspensor. Callus is again discarded if it appears.

At steps 7 and 8, modified MS-2 or DCR-2 medium contained PGRs, such as 2,4-D from about 0.1–2 $\mu$M, preferably about 1 $\mu$M, kinetin from about 0.05–1 $\mu$M, preferably 0.25 $\mu$M and BAP from about 0.05–1 $\mu$M, preferably about 0.25 $\mu$M is used. These PGR were shown to promote development of ESM to proembryo and embryo in Douglas Fir, Sugar pine, Loblolly pine, Norway spruce and other tested gymnosperms. Other PGRs and different concentration are used for induction of proembryo in other species.

Step 8 ensures that early embryos are developed. Initial process controls for maintaining stocks or for regenerating embryos is achieved by fine tuning culture medium parameters, such as temperature, time and by adjusting levels of promotory growth regulators 2,4-D, auxins, cytokinins, myo-inositol or another cyclitol(s) and nitrogenous supplements.

Cells that stain red with acetocarmine are identified and maintained by subculture because these are the source of the repetitive mitotic process of Step 7 that contributes to the development of polyembryonic clusters normally produced by cleavage during the in situ development of the zygotic seed.

These cells contribute to the development of embryos and to polyembryonic clusters by the normal cleavage process as occurs in nature.

Prospective somatic proembryos arise as a basal plant from primary embryonal cells in the ESM. As multiple embryos develop within the ESM, the primary embryonal cells proceed through true-to-type embryonal stages of development and the blue staining nuclei, which contribute to the formation of the suspensor.

Step 9 concerns the completion of the early embryonal stage with its suspensor attached. The multiple early embryos comprise the ESM because the appearance of the mass of cells is similar to that in Step 4. The ESM can now be placed in cold storage as needed and especially if continued subculture is not appropriate to maintain the ESM.

Step 10 comprises the stopping of the cleavage process so that individual cloned embryos can continue to grow and mature. Cleavage is a natural process. If the process is not controlled by the addition of abscisic acid or reduction of plant growth regulators, clonal embryos will continue to multiply. Usually the first formed embryos dominate the developmental process but the lagging reconstituted copies also develop to maturity.

Step 10 involves culture on MS-4 or DCR-4 to allow for the inhibition of cleavage polyembryony. The media are adjusted for appropriate levels plant growth regulators or promotory growth regulators as seen in Example 1 and at this stage, abscisic acid is added in the range from 0–30 $\mu$M, preferably 1–4 $\mu$M, to encourage the complete development of individual somatic embryos. The exact amounts of PGRs and ABA depends on genotype. Cell suspension in media is maintained in darkness or weak diffuse light till the late globular embryo state of development by subculture is achieved, typically at one to two week intervals. Subculture is repeated 3–4 times.

Step 11 concerns formation of elongated somatic embryos. Multiple early embryos are identified which develop within the ESM and proceed through true-to-type proembryonal stages of development to early embryo.

After subculturing three to four times on MS-4 or DCR-4 medium, the globular embryos are seen to elongate. When the globular embryos are 0.5 to 1.0 mm in diameter suspensors are already elongated. These globular embryos and suspensors, as seen in Step 9, FIG. 1, retain their affinity for red and blue stains, as described above, and can therefore be easily identified.

To effectuate this stage, embryos are placed on a filter paper support and transferred to a MS-1 or DCR-1 medium. The medium is modified to the extent that the concentration of inositol in the medium is lowered to about 100 mg/l. The culture is incubated in continuous light, preferably at 2.8, 2.0, 0.5 $\mu$w cm$^{-2}$ nm$^{-1}$ in the blue, red and far-red spectrum, in the presence of white light at about 24° C. to 25° C. The temperature and light specifications may be varied in dependence on the type of embryo but they are maintained within reasonable limits for the further development of the embryos.

When the globular embryonic masses of approximately 0.5 to 1.0 mm diameter embryo are obtained, their suspensors are already elongated. In some species, this ESM when in suspension culture (as distinct from a semisolid plate) shows signs of lignification of somatic polyembryonic clusters. This imposes some rigidity to the ESM that facilitates subculture especially in cell suspensions. If such a mass develops in prolonged suspension culture, a fabric of ESM is formed that may be difficult to separate. Globular embryos and suspensors are identified as they retain their affinity for red and blue stains, as described above.

Step 11 involves elongation of the somatic embryo (FIG. 1, Step 11) which occurs after about 7 to 8 weeks from the beginning of the cycle when the multiple cotyledons develop.

The ESM with cleaving embryos can be maintained for over one year in darkness by repeated subculture. The quality of cells and potential for embryo development are monitored by single or double diagnostic staining methods.

Step 12 concerns embryo maturation. In Step 12, the globular and elongated embryos are matured by the method and media used in *Plant Cell Reports,* 7:134–137 (1988) and in *Plant Science,* 52:299–325, (1987). The elongation and conversion to the mature embryo cotyledons (step 12) is achieved by transferring the developed embryos of stage 11 to a MS-1 or DCR-1 basal medium preferably with 0.25 (w/v) activated charcoal, 7% sucrose, 100 mg/l inositol without casein hydrolysate and glutamine. The identical embryos recovery is achieved by fine tuning of culture parameters and by adjusting levels of promotory growth regulators, and adjusting concentrations of other components, like myoinositol, ABA and a cyclitol. Maturation occurs in the presence of diffuse white light, preferably a 2.8, 2.0 and 0.5 $\mu$W cm$^{-2}$ in the red, blue and far-red spectrum, respectively.

After seven-eight weeks, somatic embryos develop multiple cotyledons and mature.

Step 12 can be, as one option, extended to stage 15, comprising conversion of the mature embryo to a plantlet, or, as a second option it can be converted to Steps 14 where the embryo is stored at low temperature in mature encapsulated state and can be revived.

Step 13 concerns encapsulation of mature embryos for longer life-time and storage, while maintaining viability and reproductive ability.

Individual embryos can be encapsulated or desiccated at this or at an earlier Step 8 for storage.

In alternative, individually converted embryos can be encapsulated for storage at 4° C. until further use.

Step 14 concerns cryogenic protection of mature and encapsulated embryo.

For long term storage, 4° C. or liquid nitrogen is used and encapsulated embryos are frozen for up to 2 years without loosing their viability and ability to be restored to their full potential. Encapsulated embryos can be converted to plantlets or fed back into the process through Steps 1–15, or reentering the Step 15.

Step 15 concerns development and conversion of mature embryo into plantlets and plants.

Step 15 involves conversion of the mature embryo into of Step 15 cotyledons and into the plantlets by planting these early embryos or cotyledons in soil and grown into plantlets that represent the new generation. Within five to six weeks from planting, complete plantlets develop from these somatic embryos. These plantlets are then transferred to containers containing sterile peat moss, vermiculite and perlite (1:2:1; w/w/w) and grown up in full light into mature plants.

Step 16 concerns production of plants by somatic polyembryogenesis for testing clones in different environments (genotype×environment) in a breeding program. Once the best interaction is found the clones can be selected and used for commercial plantings.

II. Diagnostic Techniques

One of the advantages of the current invention is that the nonembryonic and embryonic cells are easily differentiated but double-staining techniques and different stages in the process of somatic polyembryogenesis can be easily followed and distinguished by the invention's diagnostic staining techniques.

This invention has successfully demonstrated the existence of the free-nuclear stage of SPE never before seen in conifer culture. The invention further demonstrated that nuclei provide the main physical basis for totipotency in the proembryogenic process, and that the developmental fate of nuclei are divided by two major types: (1) staining red yielding somatic embryos and (2) staining blue yielding suspensors. Proembryos in SPE develop by a cleavage process involving nuclei with red-staining properties.

This invention is also based on findings that in somatic polyembryogenesis, the neocytoplasm accounts for the reactivity, optical properties and structure of embryonal cells at the first cell division, and that the neocytoplasm is an acetocarmine-reactive marker for morphogenic protoplasts.

Acetocarmine stains chromatin within the nucleoplasm of both the male and female nuclei which forms the neocytoplasm. The neocytoplasm becomes progressively organized during the first few nuclear divisions of the proembryo and during the descent of the free nuclei. This nucleocytoplasm not only stains with acetocarmine, but it also has a natural refraction under polarized light. Such refraction is present in both morphogenic as well as totipotent proembryonal and embryonal cells and protoplasts. The refraction is characterized as a weak creamy diffuse refraction or glow under polarized light. This characteristic is lacking in non-morphogenic cells. By using the acetocarmine staining and the presence of refraction, the morphogenic cells are distinguished from non-morphogenic cells.

Furthermore, the neocytoplasm of these morphogenic and totipotent cells reacts with calcaflor white and produces a bright fluorescence under UV-light (excitation wavelength 365 nm, emission >418 nm). These properties have enabled the tracing of the origin and fate of embryonal cells in the ESM. Those properties are additionally used for the determination of morphogenicity and potency of protoplasts and for distinguishing them from non-morphogenic cells.

The double staining techniques according to the invention distinguish between somatic polyembryogenesis which must be expressed according to the invention and simple polyembryogenesis which is very common in conifer species because of fertilization of several eggs. Cleavage of zygotic embryo can also occur. Double-staining of the EMS or callus from immature or mature seeds and explants helps to differentiate cells and determine the origin of the embryonic ESM in seed tissues and in slimy embryogenic callus and distinguish it from other sources.

For conifer-type proembryogenesis, the nuclei migrate as in nature. The binucleate stage and the reactivity of nuclei with stains serves as a marker for the earliest steps in somatic polyembryogenesis. Nuclei in cells migrate to one end of the cell to form the proembryos which is readily detected with acetocarmine. Since there is not yet developed a suspensor, no cells in the proembryo react with Evan's blue. Both stains can be combined to distinguish the early embryonal stage that develops from the proembryo because the early embryonal stage has a developing suspensor that reacts with Evan's blue. By contrast, callus cells and masses do not react as strongly with these stains and do not show the typical daughter-cell patterns of cell division that occur in zygotic development as in nature or as in somatic polyembryogenesis.

Nonembryogenic and embryogenic cells can be, therefore, differentiated, according to this invention, by a double-staining method.

For these diagnostic purposes, first, the callus or ESM is excised, as described in Step 2 above, and stained with 1% (w/v) acetocarmine. Then, the stained callus or ESM are heated for a few seconds over an open flame and cells are washed once with the previous culture medium. Glycerol may be added to the preparation to improve optical clarity for microscopic viewing. In alternative, acetocarmine staining can be replaced by Feulgen reaction. Second, the acetocarmine stained callus or ESM are stained with 0.5% Evan's blue for a few seconds and washed with a prior culture medium. The stained samples are evaluated as follows.

Embryogenic cells stain bright red, suspensors and nonembryogenic cells stain blue.

These staining diagnostic techniques are useful to follow organogenesis of the embryo or just to observe plant cells. Double-staining of the explant preparation is able to differentiate cells, determine the origin of the ESM in seed tissues and in slimy embryogenic callus and distinguish them from other sources.

When red and blue stains are combined sequentially, a useful nuclear-cytoplasmic diagnostic method is provided for determining the sequential stages of conifer-type somatic and zygotic polyembryogenesis. The end result is a diagnostic method that identifies proliferating proembryonal cells from all stages of the life-cycle of a tree that are suitable for mass true-to-type clonal propagation. Double staining may be followed through artificial seed formation and associated with low-temperature storage for assessment of embryonic potential until the field-testing of progeny can be completed.

III. Encapsulation for Production of Artificial Seeds

Another advantage and aspect of the invention is the method for convenient preservation and storage of the mature embryos for long periods of time without in any way affecting their ability to develop into normal functional plantlet and healthy plant.

According to this invention, proembryos, early embryos or mature embryos can be advantageously stored in an encapsulated form for long periods of time and converted from the normal mature encapsulated embryo into normal functional plantlet.

Such encapsulation is achieved by growing the proembryos or embryos on MS-4 medium, by separating each mature somatic embryo and dipping each embryo individually in a drop of sterile sodium alginate, preferably in about 1% solution of sodium alginate, followed by stirring the gelled coated embryo in 100 mM $Ca(NO_3)_2$ for about five to ten minutes. The somatic embryos encapsulated in alginate are then washed four to five times with sterile water to remove excess $Ca(NO_3)_2$ and stored in cold at about 1° C. to 4° C., or frozen (Step 14) in liquid nitrogen (−196°) in dark. After cold storage, for up to 50 to 60 days, the mature embryos which are intended to be converted to plantlets and plants are transferred to light or proembryos or early embryos are thawed and entered in the process at Step 10. In about one month, the encapsulated mature embryos produce chlorophyll and turn into normal green plantlets.

IV. Somatic Polyembryogenesis

Somatic polyembryogenesis according to the invention is useful for clonal propagation of gymnosperms, plants lacking flowers and reproducing by seeds borne naked in a special structure, such as a cone. The invention is particularly useful for somatic polyembryogenesis of conifers, that is cone-bearing trees such as pines, spruces and cypresses. One group of trees where the invention is useful are trees of genus Pinus, such as Pinus Lambertiana (Sugar Pine); Pinus Taeda (Loblolly Pine); Aristata Engelm (Hickory Pine); Monterumae Lambertiana (Rough-Barked Mexican Pine); Monticola Douglas (Western White Pine); Pinus insignis Douglas (Monterey Pine); *P. sitchensis* (sitka spruce), P. glauca (white spruce), P. Engelmanni (Engelman spruce). Another group where the invention is useful are trees of Genus Picea, such as Picea Abies (Norway spruce), A. concolor (Colorado spruce), A. Fraseri (Balsam fir).

Still another group of trees where the invention is useful are trees of genus Pseudotsuga, such as Pseudotsuga Menziesii (Douglas Fir); Pseudotsuga Japonica (Japanese Fir); and Pseudotsuga Macrocurpa (Big-Cone spruce) and Sequoia Sempervirens. Other species for each genus are listed in *Hortus Third*, A Concise Dictionary of Plants Cultivated in the United States and Canada, MacMillan Publishing Co., Inc. New York.

Somatic polyembryogenesis is superior to other known method of reproduction such as simple polyembryogenesis, sporophytic false polyembryogeny and gametophytic false polyembryony. The origins of the embryos and recovered genotypes in each of these polyembryogenic groups are illustrated in Table 1.

TABLE 1

The Origins and Characteristics of
Various Types of Polyembryony

| POLYEMBRYO-GENY TYPES | ORIGINS | RECOVERED GENOTYPES |
|---|---|---|
| Simple (Polyzygotic) | Different eggs in same megagametophyte | Variable, due to fertilization and self-fertilization (new generation) |
| Cleavage or budding (Zygotic and somatic polyembryony) | Reconstitution of multiple embryos by cleavage division of a single proembryo or by budding of embryonal tubes and suspensors, often with a free-nuclear stage. | Identical, (new generation) |
| Sporophytic (False polyembryony or reproductive regeneration) | 1. Multiple megagametophytes in an ovule. | Variable, based on material genotype |
| | 2. Budding of nucellus, etc. | " |
| | 3. Induction on explants from embryonic, juvenile and/or mature phases. | Often precocious expressions. and variable (somaclonal) based on source genotype. |
| Gametophytic (False polyembryony or reproductive regeneration | 1. Induction of haploid female gametophytes. | Variable, based on maternal genotype. |
| | 2. Induction of haploid male gametophytes (unreported). | Variable, based on paternal genotypes and possible polyspermy. |

As seen in Table 1, the only recovered genotype which is identical in the new generation is somatic polyembryony, whether zygotic or somatic. All other polyembryony process result in variable recovered genotypes whether due to fertilization, based on maternal or paternal genotypes or for other reasons.

Process and method for somatic polyembryogenesis is illustrated in FIG. 1, which shows different stages of the process and the development of the ESM from a mature or immature seed or explant tissue removed from the selected tree genotype. The process continues through stages of culturing the ESM for growth and testing the grown ESM, using double staining techniques for distinguishing nonembryogenic callus and embryogenic ESM tissue able to develop into proembryo when cultured as cell, suspension in specific nutrient media in the presence of specific concentrations of promotory growth regulators, progressing through the free nuclear stage and nuclear migration to the stage where the proembryo and early embryo appears and is multiplied by repeated division, through the induction of cleavage polyembryonic mass into the stage where the globular embryo are converted into elongated somatic embryos to be matured and further incubated growth inducing conditions into stage where roots and shoots appear and the embryo grows into the plantlet and plant. Such grown plants are useful for commercial planting or for bleeding tests and selection of the best genotype to be reproduced.

The somatic polyembryogenesis has been tested on representative species of gymnosperm, as conifers, family Pinaceae. Testing included species from genus pinus, such as Sugar pine (*Pinus lambertiana*), Loblolly pine (*Pinus Taeda*), Genus picea, such as Norway spruce (*Picea abies*), Genus Pseudotsuga, such as Douglas Fir (*Pseudotsuga menziesii*).

The SPE process begins with a selection of a superior tree of the above family Pinaceae growing in the forest. Many of these species, as described above and below, are impossible to asexually propagate and under the normal conditions, these species propagate solely sexually. Sexual reproduction by the pollinated pine cone leads to genotypic variation.

To the contrary, the current invention leads to production of somatic identical embryos and plants from either the mature seed collected from an open pollinated pine cone (Steps 1–16) or from the meristematic tissue, explant, from either the stems or roots (Steps A and B).

FIG. 2 represents somatic polyembryogenesis of the cleavage. type in coniferons species. Specifically, FIG. 2 shows recovery of free and encapsulated somatic embryos of Norway spruce by SPE, free nuclear stage in Loblolly pine, Douglas fir and Sugar pine. For conifers, the recovery of multiple embryos from cells in a rescued EMS follows the sequence shown in FIG. 2 and also in FIG. 3.

Figure 2A:
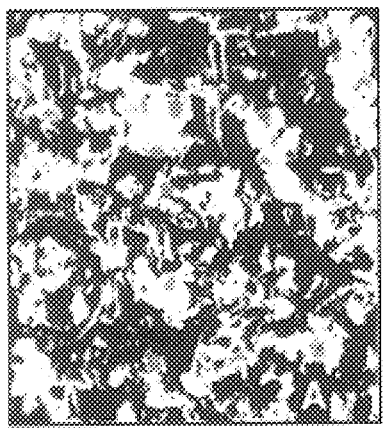
FIGS. 2A–2H are photographs showing somatic polyembryogenesis of the budding type in coniferous species.

FIG. 2A is a photograph showing a loblolly pine cell suspension culture of an embryonal-suspensor mass (ESM) stained with acetocarmine to show centers of new embryo formation. Enhancement is ×10. FIG. 2 corresponds to Step 6 in FIG. 1.

Figure 2B:
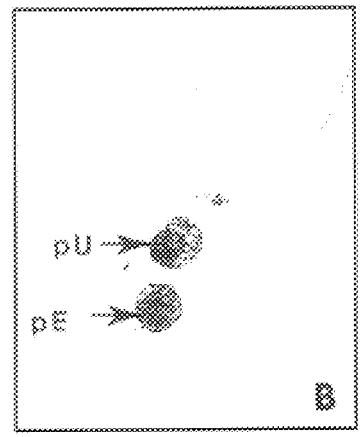

FIG. 2B is a photograph illustrating a free nuclear stage in a budding embryonal tube cell of loblolly pine. Nuclei migrate to form the proembryo (pE) and upper tier of suspensor (pU). The elongated budding cell is derived from a rescued ESM of loblolly pine. Free nuclei and their adhering cytoplasm are stained red with acetocarmine.

Enhanced ×42. FIG. 2B corresponds to Step 7 in FIG. 1.

Figure 2C:
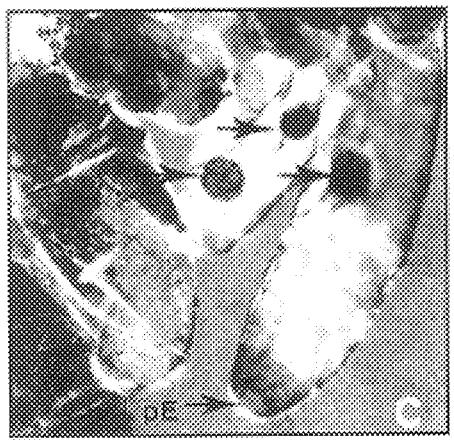

FIG. 2C is a photograph showing an ESM of Douglas Fir stained with Orcein to reveal the free nuclear stage and plant migration of nuclei after staining (arrows) in embryonal tube cells undergoing the cleavage process. Enhanced ×42.

Figure 2D:
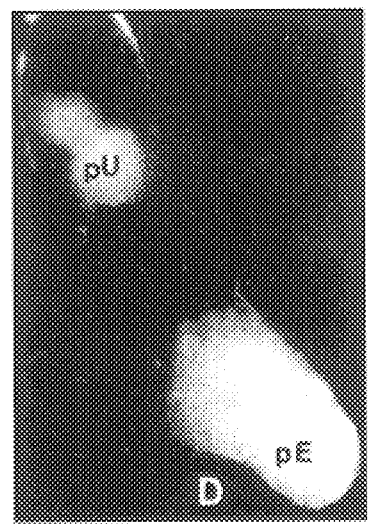

FIG. 2D is a photograph showing a lobbing embryonal tube of Douglas fir showing the formation of neocytoplasm stem green fluorescence after staining with calcaflor around migrating proembryo pE and pU nuclei. Enhanced ×42. FIGS. 2C and 2D correspond to Step 7, FIG. 1.

Figure 2E:
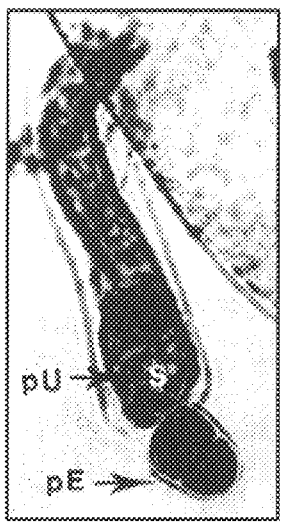

FIG. 2E is a photograph showing proembryo and suspensor formed after nuclear migration. The proembryo stains red with acetocarmine and the suspensor is permeable to Evan's blue. Enhanced ×40. FIG. 2E corresponds to Step 8, FIG. 1.

Figure 2F:
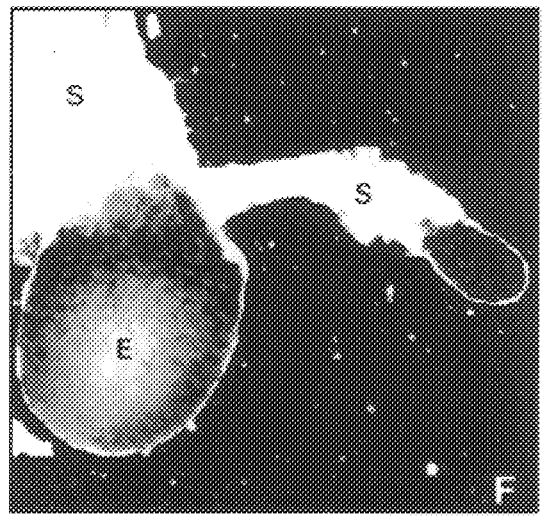

FIG. F is a photograph of an ESM obtained for sugar pine, showing a large embryo (E) with a mass of suspensor cell(s). Another smaller embryo emerges and develops off the flanks of the main embryo. The embryonal-suspensor mass is stained with acetocarmine to reveal developing embryos. Enhanced ×10. FIG. 2F corresponds to Step 8, FIG. 1.

Figure 2G:
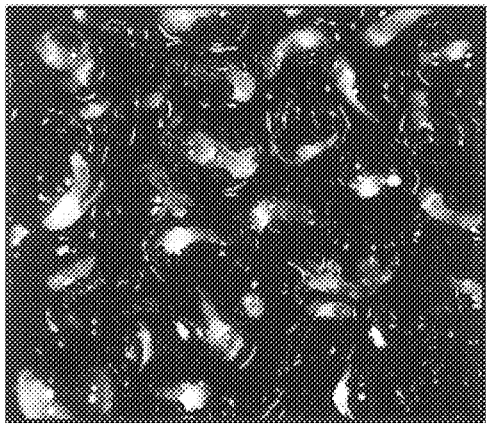

FIG. 2G is a photograph showing somatic embryos (2 to 3 mm long) of Norway spruce encapsulated in a alginate gel for storage and handling. Embryos have become green through exposure to light. FIG. 2G corresponds to Step 13 in FIG. 1.

Figure 2H:

FIG. 2H is a photograph showing Norway spruce plantlets can be recovered at a frequency of a 25 plantlets per ml of cell suspension culture. Plantlet sizes vary from 1 to 1.5 cm in length. A light-sensitive layer of black coleorrhizal cells cover a light brown root that prepares the plant for soil (arrow). FIG. 2H corresponds to Step 15 in FIG. 1.

FIG. 3 illustrates somatic cleavage and budding polyembryogenesis in conifers.

Figure 3A:
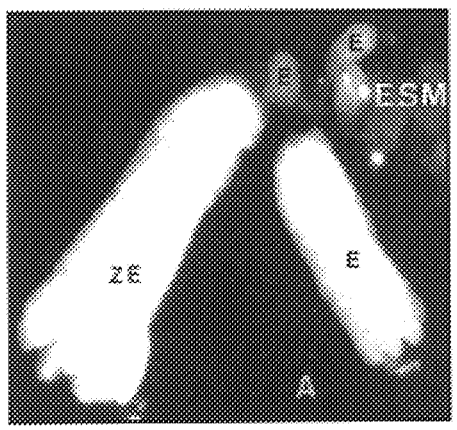
FIGS. 3A–3H are photographs showing somatic cleavage and budding polyembryogenesis in conifers.

FIG. 3A is a photograph of a rescued ESM from 5-year-old seed of sugar pine. Embryos in the mass represent a controlled cross between two blister rust-resistant parents. The main zygotic embryo (ZE) can be recovered together with others at earlier development stages. The embryos (E) are formed by the natural polyembryonic process, which is exploited by culturing cells of the mass in suspension cultures. Enlarged ×9. FIG. 3A corresponds to Step 2, FIG. 1.

Figure 3B:
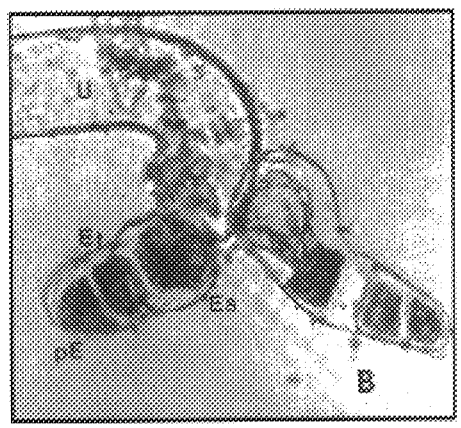

FIG. 3B is a photograph of two proembryos of sugar pine in suspension culture that have formed by budding polyembryony. pE is a proembryonal cell, Et is a embryonal tube, Es is a embryonal suspensor. Et and Es cells bud only once to produce a free nuclear stage that resets development to the point just after fertilization. Enhanced ×27.

Figure 3C:
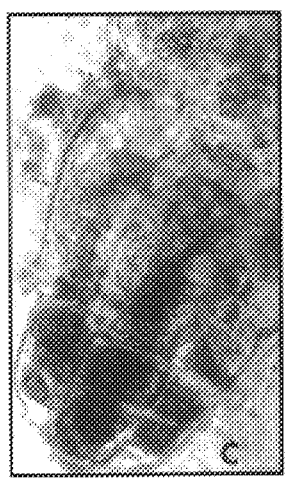

FIG. 3C is a photograph of a sugar pine proembryo with the characteristic tier of daughter cells. Enhanced ×29. FIG. 3C corresponds to the proembryo and early embryo of Step 8, FIG. 1.

Figure 3D:
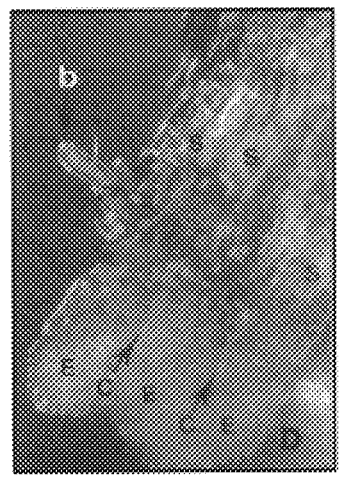

FIG. 3D is a photograph representing individual but adhering Douglas fir somatic embryos reconstituted by longitudinal cleavage from an ESM. Cleavage sites (C) appear between individual embryos (E) and suspensors (S). The arrow at b indicates the possible start of budding polyembryony. Enhanced ×16. FIG. 3D corresponds to cleavage of Step 10, FIG. 1.

Figure 3E:

FIG. 3E is a photograph of cleavage polyembryony in Douglas fir cell suspension cultures, as revealed by acetocarmine and Evan's blue staining. Proembryonal cells have cleaved (C) longitudinally to form a mass of 12 or more adhering embryos with their supporting suspensor system. Not all cleavage products are at the same stage of development. The adherence of embryos can be prevented by adding abscisic acid in the medium. Enhanced ×43. FIG. 3E corresponds to Step 10, FIG. 1.

Figure 3F:

FIG. 3F is a photograph showing budding polyembryony in loblolly pine suspension culture. Cells have been stained with acetocarmine and Evan's blue. Embryo (E) is visible at the end of suspensor (S). The suspensor (S) system ends to lignify upon agitation and adds support the multiplicative polyembryogenic process. Enhanced ×39. FIG. 3F corresponds to Step 6, FIG. 1.

Figure 3G:
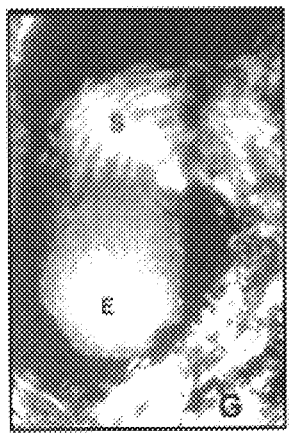

FIG. 3G is a photograph illustrating the development of individual Douglas fir embryos which can be promoted with the addition of abscisic acid inhibiting the cleavage process. Embryos (unstained) are grown to this stage in darkness nad then exposed to light as cotyledons emerge. Enlarged ×16. FIG. 3G corresponds to Step 9, FIG. 1.

Figure 3H:
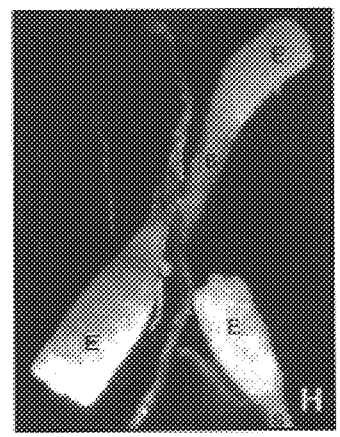

FIG. 3H is a photograph of unstained somatic embryos of Douglas fir produced after one month in cell suspension culture showing the start of cotyledon formation. Enlarged ×19. FIG. 3H corresponds to Step 12, FIG. 1.

FIG. 4 illustrates process for somatic polyembryogenesis from explant tissues as seen in FIG. 1, Steps A and B.

Figure 4A:
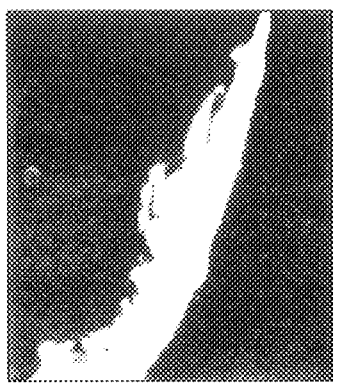
FIGS. 4A–4F are photographs showing somatic polyembryogenesis in Douglas fir.

FIG. 4A is a photograph of a mucilage covering an excised leaf (Step A) from rejuvenated cutting obtained from a mature Douglas fir when grown in darkness on MS-1 modified medium containing 2,4-D and BAP supplemented with α-glutamine. The presence of mucilage is an indication for production of embryogenic callus. The FIG. 4A corresponds to Step 4, figure where the callus is discarded and ESM is retained. Enlarged ×60.

Figure 4B:

FIG. 4B is a photograph showing a callus which forms on the leaf surface and contains embryogenic cells that can be detected by a presence of red stained tissue after acetocarmine staining. Double staining with Evan's blue shows blue nonembryogenic cells. In the right hand corner is a polyacrylamide gel (12.5%) with separated protein stained with acetocarmine. The proteins found in embryogenic cells react and their molecular weights in kDA is shown on the scale at the right. FIG. 4B corresponds to Step 4 derived from Step B in FIG. 1. Enlarged ×125.

Figure 4C:
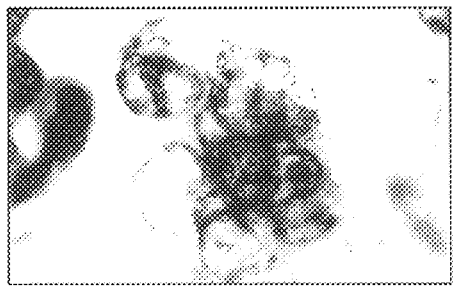

FIG. 4C is a photograph of close-up view of induced embryogenic cells in leaf that will form an ESM. FIG. 4C corresponds to Step 4 in FIG. 1. Enlarged ×125.

Figure 4D:

FIG. 4D is a photograph corresponding to Step 8 in FIG. 1, showing red clusters of cells at the proembryo stage that will next produce an axial tier suspensor. Enlarged ×200.

Figure 4E:

FIG. 4E is a photograph of early embryo stained with acetocarmine, having elongated cells in the axial tier. Arrow points to a binucleate cell that is equivalent to the binucleate egg in conifers. FIG. 4E corresponds to Step 8 in FIG. 1. Enlarged ×195.

Figure 4F:
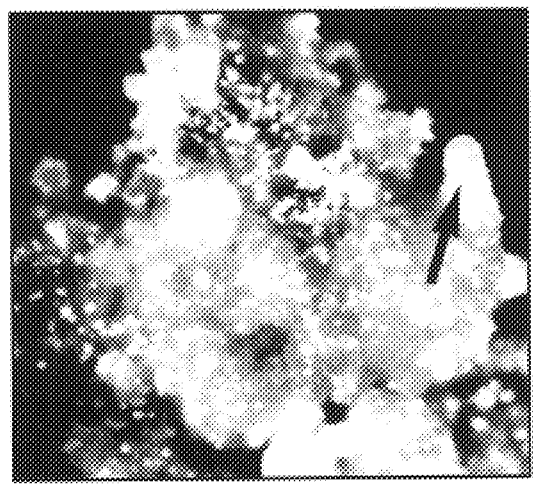

FIG. 4F is a photograph of elongated embryo after 3–4 months under exposure to white light when cells of the leaf grow out as a brown callus which is discarded. The viable somatic embryos (arrow) of various sizes are white starting to turn green. Enlarged ×20. FIG. 4F corresponds to Steps 11 and 12 in FIG. 1.

Figure 5:
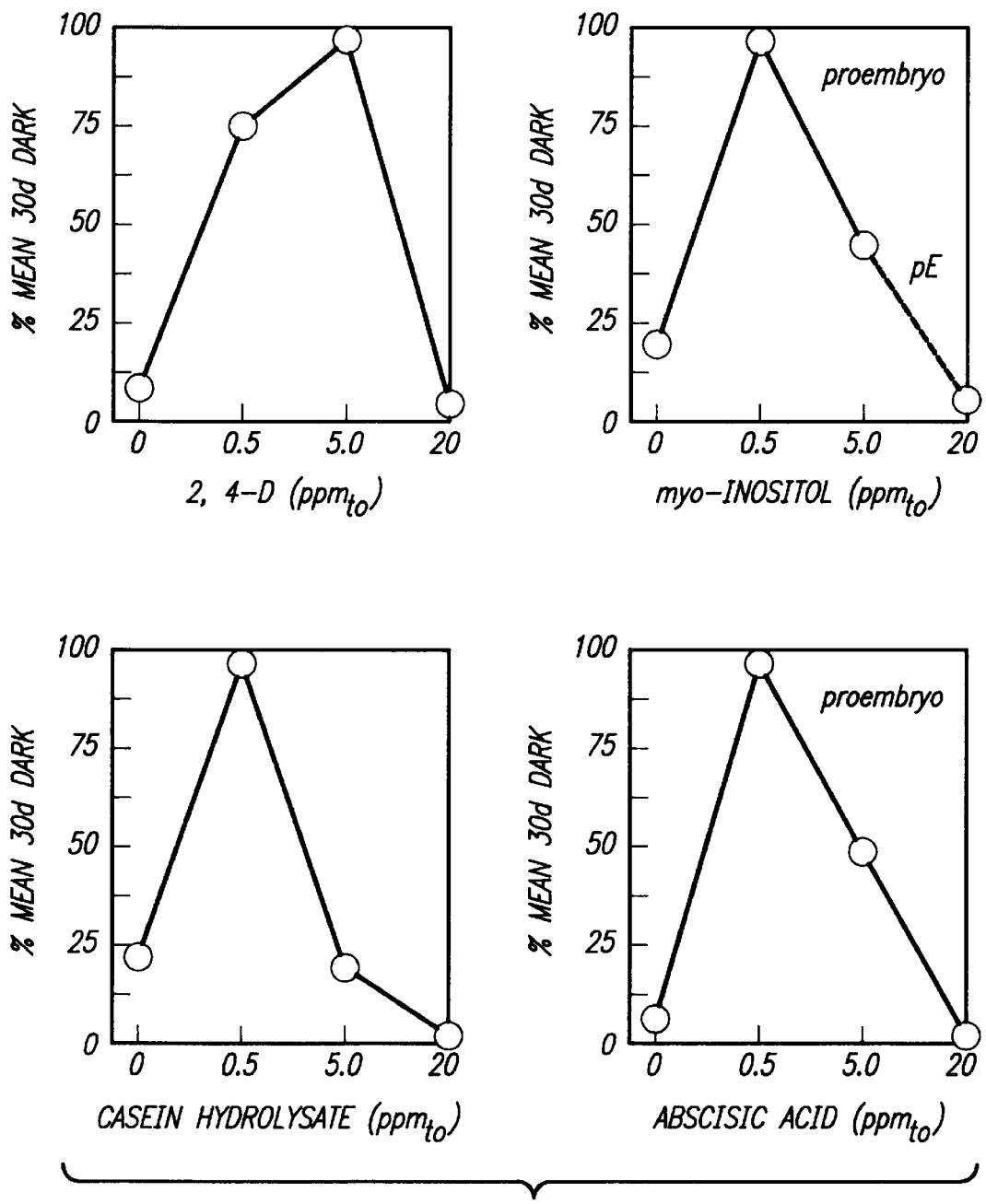
FIG. 5 shows graphs illustrating embryo recovery rate in the presence of various promotory growth regulators.

FIG. 5 illustrates the early embryo recovery rate in the presence of various promotory growth regulators after 30 days incubation in the basal medium supplemented with 2,4-D, myo-inositol, casein hydrolysate and abscisic acid. Hundred percent recovery rate for embryo incubated in the presence of 2,4-D was achieved with 5 mg/l of medium.

Hundred percent recovery rate for embryo incubated in the presence of myo-inositol was achieved with 100 mg/l of medium. Hundred percent recovery rate for embryo incubated in the presence of casein hydrolysate was achieved with 100 mg/l of medium. Abscisic acid was able to achieve the 100% recovery rate at 3.8 $\mu$M concentration.

The dotted line from 1000 to 5000 mg/l indicates a preponderance of cells ($p_{EL}$) that will give proembryos in the medium.

Somatic polyembryogenesis was tested and successfully achieved in several conifers.

Somatic polyembryogenesis in Sugar pine was achieved by using procedure according to Example 2.

Somatic polyembryogenesis in Norway spruce was achieved by using procedure according to Example 3.

Somatic polyembryogenesis in Loblolly pine was achieved by using procedure according to Example 4.

Somatic polyembryogenesis in Douglas fir was achieved by using procedure according to Example 5.

The effect of abscisic acid in somatic polyembryogenesis is illustrated in Example 6. Abscisic acid inhibits polyembryogenesis in that it inhibits further cleavage process of Step 11 and in this way prevents adherence of embryos to their suspensor and their maturation.

Somatic polyembryogenesis in embryonic cell masses of various conifers achieved after regeneration from liquid nitrogen is illustrated in Example 8.

Induction of morphogenesis in explants in contact with ESM in various conifers is illustrated in Example 9.

Successful somatic polyembryogenesis as shown in the above conifers is surprising and unexpected as under normal circumstances and without involving the method for somatic polyembryogenesis of the current invention, the recovery of healthy and totipotent suspensor tissue from five-year-old seeds is difficult and unpredictable. The success of such recovery often depends upon seeds origin and storage. The current invention overcame the problems encountered before, by providing a method allowing a recovery of a much higher percentage of embryonic cells obtained by culturing the suspensor tissue from immature seeds. This finding is supported and evidenced by the presence of increased number of cytoplasmically dense cells with large nuclei that stain with acetocarmine totally, that is both nuclei and cytoplasm are stained. The totipotent embryonic cells from all species were found to be very similar to polyembryogenic nucellar tissue in Citrus and also to zygotic embryos in vitro.

The potential for somatic polyembryogenesis (SPE) is traced not to a callus but to the nuclei of proembryonic cells in an ESM. This is supported by acetocarmine and Feulgen staining and by fluorescence properties of cells under the light microscope. In short, for the first time, it is shown that the origin of SPE is not a callus but somatic cells in the ESM and that ESM can be advantageously used for conifer-type somatic polyembryogenesis.

The invention reveals the essentiality of the free-nuclear stages of proembryony and recognizes the importance of color coded nuclei (using a double-staining diagnostic test) in the process. Under the conditions of the invention, nuclei of the ESM repeatedly divide to maintain or establish a free-nuclear stage and to produce repetitively the equivalent in nature of cleavage polyembryogenesis.

In explants from immature seeds, the presence of the female gametophyte attached to the suspensor cells aids the establishment of the embryonal-suspensor mass and the development of somatic polyembryogenesis. Further improvement in the performance of the current embryogenic process is shown by removal of the dominant embryo. Removal of such dominant embryo releases the growth of smaller embryos and the somatic polyembryogenesis remains repetitive as long as the ESM is maintained on the 2,4-D medium.

Mature embryos produced by SPE according to the invention, transferred to the basal medium without supplements and with activated charcoal under continuous light produce complete plantlets within forty days at a low (1%–2%) conversion in the blue, red and far red range. This process is further improved with addition of abscisic acid which inhibits the cleavage process and minimizes the recovery of embryos that remain adhered together, and by transfer of mature embryos to a container with a porous substrate, such as cheesecloth or polyester fabric, that provides surface and aeration for separated embryos to develop further.

In a free-nuclear proembryonic stage in cells suspension cultures four free nuclei are observed. During the late free-nuclear proembryonic stage, the red stained proembryonal nucleus migrates to the cell wall at the location of the emergence of the proembryo. The free-nuclear stage is followed by early embryogeny which exhibits early division patterns of proembryo by showing red staining of cells and by blue staining of elongation of a suspensor. Some suspensors have nuclei which retain an affinity for acetocarmine. These embryos have the potential of producing somatic embryos. By contrast, the direct production of nonembryogenic callus from the proliferative embryonal-suspensor mass is not evident.

Somatic proembryogenesis begins with the migration and segregation of nuclei in proembryonal cells similar to zygotic embryogenesis. While actual migration of the nuclei was not observed, however, photographs of the somatic proembryo cells indicate that wherever a new somatic proembryo emerges, the red staining nuclei are always very closely associated with the cell wall at one pole of the initially multinuclear cell. Mitosis splits off proembryonal cells with large nuclei thereby contributing to the vivid red color of the prospective embryo.

In conifer-type zygotic embryogenesis, the free-nuclear stage is initiated by the first zygotic division to produce the proembryonal tier of cells. The first division results in two and then four free-nuclei. These nuclei migrate or are pulled to the base of the archegonia where they partially wall off and initiate the proembryo. In somatic polyembryogenesis, repetitive divisions were also shown to result in the initial free-nuclear stage. Mitosis in the embryonal-suspensor mass contributed to the multiplicity of embryos in the polyembryogenic process. For loblolly pine, somatic polyembryogenesis was repeated for over fourteen months. The observed developmental patterns were consistent with zygotic pine polyembryony in vitro, described in *Am. J. Bot.*, 49:327–333 (1962).

The origin of the repetitive or cleavage phenomenon was related to mitosis and the fate of acetocarmine and to the fate of Feulgen-positive nuclei in somatic proembryonal cells in cell suspension cultures. Based on the staining results, the embryonal-suspensor mass was shown to be not a callus but a cellular array of significant true-to-type developmental potential, provided that the conditions of the culture resembled those of the true environment of the egg. Such conditions were provided by the modified basal media according to the invention. Nonembryogenic callus shows none of the observed staining or developmental properties under the same conditions. The staining and developmental nuclear characteristics were found in Douglas-fir, Norway spruce, Loblolly pine and Sugar pine.

When red and blue stains are combined sequentially, a useful nuclear-cytoplasmic diagnostic method is provided for determining the sequential stages of conifer-type somatic and zygotic polyembryogenesis. The end result is a diagnostic method that is able to identify proliferating proembryonal cells from all stages of the life-cycle of a tree that are suitable for mass true-to-type clonal propagation.

Double staining technique according to the invention is further enhanced, through artificial seed formation, with low-temperature storage for assessment of embryonic potential until the field-testing of progeny can be completed.

During the development of this invention, it was determined that by using the basal media of the invention advantageously complemented with the PGRs, the suspensor and suspensor mass is able to provide the connection and much of the nourishment for the developing embryo. This resulted in the development of one to five plantlets per gram of fresh cell mass on paper bridges. Over 1000 acetocarmine staining proembryos were recovered from 100 ml of cell suspensions.

UTILITY

The invention described herein is the first to ever discover and describe true somatic polyembryogenesis where the origin of the adventive embryos are from free nuclear cells identical to that found in the zygote and proembryo of developing seeds. In mature seeds and other explant sources, an ESM is recovered that restores these original type of zygotic and proembryonal cells that have the capacity to cleave and produce multiple embryos by cleavage polyembryony. The somatic polyembryogenesis according to the invention is extremely true-to-type both in temporal and developmental terms resulting in the production of a large array of suspensor cells and embryos with multiple cotyledons.

The present invention encompasses a process for the production of somatic embryos that are conifer-type in basal plan of development through the use of cell and tissue culture using liquid suspensions. According to the current invention, mass production of plantlets for afforestation, reforestation and for the ornamental commercial use can be activated.

This invention advances the existing technology by using mature seeds up to five years old from controlled parents and by producing normal or hybrid embryos. The potential for somatic polyembryogenesis (SPE) depends on the nuclei of proembryonic cells in an ESM. This is evidenced by diagnostic tests using acetocarmine and Feulgen staining and fluorescence properties of cells under the light microscope. Using the diagnostic staining, for the first time, it was discovered that the origin of SPE is not callus but somatic cells in the ESM and that such somatic polyembryogenesis is conifer-type SPE.

This invention has demonstrated that it is possible, by the current invention to achieve:

(1) The free-nuclear stage never before seen in conifer culture. Free nuclear divisions provide the main physical basis for cleavage polyembryony in the multiplication process.

(2) The understanding there were two types of developmental nuclei divided by their ability to stain red, yielding somatic embryos and blue, yielding suspensors.

(3) Development of proembryos in SPE by a cleavage process involving nuclei with red-staining properties. This process differs from simple polyembryogenesis where embryos develop from different eggs or somatic embryogenesis where nucellar tissues or protodermal cells are employed and where the progeny represents the mother tree. SPE represents the potential of the new generation.

(4) Repetitive SPE that could be maintained with auxins and cytokinins on specially formulated and supplemented media.

(5) Completed recovery of embryos with conifers such as Douglas-fir, Sugar pine, Loblolly pine and Norway spruce and production of plants.

(6) Improvement of selectivity and efficiency of the SPE process, followed by storage and conversion of embryos by using multiple diagnostic tests at strategic SPE steps.

(7) The extended storage of somatic polyembryos at low temperatures using an artificial coat. Normally coating is used to construct artificial seeds and not to achieve low temperature storage.

(8) All steps in the laboratory setting for SPE as referenced to what occurs in nature. The basal plan of "conifer-type" processes represents true-to-type embryogeny and demonstrated and placed emphasis on the repetitive cleavage origins of embryos from ESM by the cleavage process.

(9) The cell suspension cultures (as opposed to callus cultures) utilizing the lignification and differentiation of suspensor cells to provide hydrodynamic stability to the developing embryonal masses.

(10) Design of the above parameters into a unique overall process which correctly recognizes the origin and development of true-to-type repetitive conifer-type SPE and provides conditions allowing such a process to proceed in controlled laboratory setting.

The current invention provides several advantages over the state of the art in that, among others, it can distinguish and consequently address true somatic polyembryogenesis, in that it allows a recovery of healthy and functional plants from several years old seeds, in that complete functional plantlets can be produced within about forty days from selected embryo, and in that the fully embryogenic and non-embryogenic cells can be diagnosed and distinguished.

Consequently, the first advantage of this invention is that all of the embryos in the seed ESM capable of SPE are genetically identical and any embryo which is capable of SPE produces only genetically identical embryos.

The second advantage of this invention is that zygotic embryos and embryos of an EMS in the seed which are capable of SPE, whether by cleavage or free nuclear budding, can be detected and their SPE capability determined by double staining techniques and microscopic examination according to the invention.

The third advantage of this invention is SPE can be initiated in mature or immature seeds or explant tissues from selected and controlled genotype crosses and this selected genotype can be almost unlimitedly propagated with very minor, if any, genotype changes into large numbers of embryos, plantlets and plants.

The fourth advantage of this invention is initiation of the free-nuclear stage divisions in conifer culture, never before seen, which divisions provide the main physical basis for cleavage polyembryony in the multiplication process.

EXAMPLE 1

Culture Media

This example illustrates culture media used for generation of somatic embryos and plantlets.

A. Basal Media

1. Basal Murashige-SkooQ Medium

Basal Murashige-Skoog (MS) medium is according to *Physiol. Plant*, 15:473 (1962).

The following represent modifications of basal MS medium:

Murashige-Skoog-1 Medium

Murashige-Skoog-1 (MS-1) medium represents modification 1, half-strength basal MS medium with added casein hydrolysate (500 mg/l), L-glutamine (450 mg/l), myoinositol (1000 mg/l), sucrose 3%.

Murashige-Skoog-2 Medium

MS-1 with added 2,4-D ($15 \times 10^{-5}$M), kinetin and $N^6$-benzyladenine ($2 \times 10^{-5}$M) each.

Murashige-Skoog-3 Medium

MS-1 with added 2,4-D ($15 \times 10^{-6}$M), kinetin and $N^6$-benzyladenine ($2 \times 10^{-6}$M) each.

Murashige-Skoog-4 Medium

MS-1 with added NAA ($1 \times 10^{-6}$), kinetin and $N^6$-benzyladenine ($2 \times 10^{-5}$M) each.

2. Basal DCR Medium

Basal DCR medium is distinctively different from MS and has the composition cited in *Plant Cell Reports* 4: 177 (1985).

| | mg/L |
|---|---|
| $NH_4NO_3$ | 400 |
| $KNO_3$ | 340 |
| $Ca(NO_3)_2 4H_2O$ | 556 |
| $KH_2PO_4$ | 170 |
| $MgSO_4.7H_2O$ | 370 |
| $CaCl_2.2H_2O$ | 85 |
| $H_3BO_3$ | 6.2 |
| $MnSO_4.H_2O$ | 22.3 |
| $ZnSO_4.H_2O$ | 8.6 |
| $CuSO_4.5H_2O$ | 0.25 |
| KI | 0.83 |
| $FeSO_4.7H_2O$ | 27.8 |
| $Na_2EDTA$ | 37.3 |
| $CoCl_2.6H_2O$ | 0.025 |
| $NiCl_2$ | 0.025 |
| $NaMoO_4.2H_2O$ | 0.25 |
| Thiamine.HCl | 1.0 |
| Pyridoxine.HCl | 0.5 |
| Nicotinic Acid | 0.5 |
| Glycine | 2.0 |
| myo-Inositol | 200 |
| Sucrose | 30 g/L |

The following represent modification of a basal DCR medium:

DCR-1 Medium

Half-strength basal DCR medium with added casein hydrolysate (500 mg/l), 1-glutamine (450 mg/l), myoinositol (1000 mg/l) and sucrose 3%.

DCR-2 Medium

DCR-1 medium with added 2,4-D ($5 \times 10^{-5}$ M), kinetin and $N^6$-benzyladenine ($2 \times 10^{-5}$ M) each.

DCR-3 Medium

DCR-1 medium with added 2,4-D ($5 \times 10^{-6}$ M), kinetin and $N^6$-benzyladenine ($2 \times 10^{-6}$ M) each.

DCR-4 Medium

DCR-1 medium with added NAA ($1 \times 10^{-6}$ M), kinetin and $N^6$-benzyladenine ($2 \times 10^{-5}$ M).

MS or DCR medium is adjusted to pH 5.7 or 6.0, respectively with KC1 and KOH, Bacto agar 0.6% is added (w/v) and autoclaved (1·1 kg cm²) at 121° C. for 20 minutes.

b. Specific Media

Douglas Fir—DMH Media

For preparation of 1 liter of DMH media, which is based on DCR modified medium diluted 1:1, v/v.

| DCR Media (0.5%) | | | |
|---|---|---|---|
| Nitrate | (50% Stock) | 10 | ml |
| Sulfate | (50% Stock) | 10 | ml |
| PBMO | (50% Stock) | 10 | ml |
| Halide | (50% Stock) | 10 | ml |
| FeEDTA | (1000% Stock) | 5 | ml |
| Vitamin | (1000% Stock) | 1 | ml |
| Sucrose | (3%) | 1 | ml |
| Inositol | | 1000 | mg |
| Casein Hydrolysate | | 500 | mg |
| L-glutamine | | 450 | mg |
| 2,4-D | (1 µmole/ml stock) | 5 | ml |
| Kinetin | (1 µmole/ml stock) | 2 | ml |
| BAP | (1 µmole/ml stock) | 2 | ml |
| Agar | | 0.6% | |
| pH 5.75 | | | |

Water up to 1000 ml. DMH media is adjusted to pH 5.75 before autoclaving.

Loblolly Pine-LP Media

For the preparation of 1 liter of LP media which is LP media diluted 1:1 (v/v). LP Media (0.5%).

| LP Medium | 10% Stock | 50 | ml |
|---|---|---|---|
| FeEDTA | 100% Stock | 5 | ml |
| Vitamin | 1000% Stock | 1 | ml |
| Sucrose | | 3% | |
| Inositol | | 1000 | mg |
| Casein acid hydrolysate | | 500 | mg |
| L-glutamine | | 450 | mg |
| 2,4-D | 1 µmole/ml Stock | 5 | ml |
| Kinetin | 1 µmole/ml Stock | 2 | |
| BAP | 1 µmole/ml Stock | 2 | ml |
| Agar | | 0.6% | |
| pH 5.7 | | | |

Water up to 1000 ml. LP media is adjusted to pH 5.70 before autoclaving.

Picea Abies-BMH Media

For the preparation of 1 liter of BMH media which is based on the original MS medium that is diluted 1:1, v/v.

| (0.5% MS Media) | | | |
|---|---|---|---|
| Macro Salts | 4% Stock | 125 | ml |
| FeEDTA | 100% Stock | 5 | ml |
| Vitamin | 1000% Stock | 1 | ml |
| Micro Salts | 1000% Stock | 0.5 | ml |
| Sucrose | | 3% | |
| Inositol | | 1000 | mg |
| Casein Hydrolysate | | 500 | mg |
| L-glutamine | | 450 | mg |
| 2,4-D | 1 µmole/ml stock | 5 | ml |
| Kinetin | 1 µmole/ml stock | 2 | ml |
| BAP | 1 µmole/ml stock | 2 | ml |
| Agar | | 0.6% | |
| pH 5.7 | | | |

Water up to 1000 ml. BMH media is adjusted to pH 5.7 before autoclaving.

Stock Solutions

Macro Salts–4% Stock

For the preparation of 4 liters of 4% macro salt stock solution.

| $NH_4NO_3$ | 8.812 g |
|---|---|
| $KNO_3$ | 74.784 g |
| $CaCl_2$ | 7.040 g |
| $MgSO_4$—$7H_2O$ | 5.920 g |
| $KH_2PO_4$ | 2.720 g |

Water up to 4000 ml.

Micro Salts—1000% Stock

For the preparation of 100 ml of 1000% micro salt stock solution.

| $H_3BO_3$ | 0.620 g |
|---|---|
| $MnSO_4$—$H_2O$ | 1.690 g |
| $ZnSO_4$—$7H_2O$ | 0.860 g |
| Potassium iodide (KI) | 0.083 g |
| $NaMoO_4$—$H_2O$ | 0.025 g |
| $CuSO_4$—$5H_2O$ | 0.0025 g |
| $CaCl_2$—$6H_2O$ | 0.0025 g |

Water up to 100 ml. Store as a filter sterilized solution.

Nitrate 50%-Stock

To prepare 1 liter of 50% sulfate stock solution.

| $NH_4NO_3$ | 20.0 g |
|---|---|
| $Ca(NO_3)_2$—$4H_2O$ | 27.8 g |

-continued

| | |
|---|---|
| $KNO_3$ | 17.0 g |

Water up to 1000 ml.
Sulfate 50%-Stock
To prepare 1 liter of 50% sulfate stock solution.

| | |
|---|---|
| $MgSO_4$—$7H_2O$ | 18.5 g |
| $MnSO_4$—$H_2O$ | 1.115 g |
| $ZnSO_4$—$7H_2O$ | 0.43 g |
| $CaSO_4$—$5H_2O$ | 0.0125 g |

Water up to 1000 ml.
Halide 50% Stock
To prepare 1 liter of 50% halide stock solution.

| | |
|---|---|
| CaCl—$2H_2O$ | 5.5 g |
| KI | 0.0415 g |
| CaCl—$6H_2O$ | 0.00125 g |
| NiCl | 0.00125 g |

Water up to 1000 ml.
PBMO Stock 50% Stock
To Prepare 1 liter of 50% phosphate, borate, molybdenate stock solution.

| | |
|---|---|
| $KH_2PO_4$ | 8.5 g |
| $H_3BO_3$ | 0.31 g |
| $Na_2MoO_4$ | 0.0125 g |

BAP Stock-1 µmole/ml
To prepare 100 ml of BAP:

| | |
|---|---|
| BAP | 22.25 mg |
| HCl 0.1 N | 2 ml |

Dissolved BAP in 2 ml of 0.1N HCl. Water up to 100 ml.
Kinetin Stock
To prepare 100 ml of kinetin stock solution:

| | |
|---|---|
| Kinetin | 22.54 mg |
| KOH | 2 ml |

Dissolve kinetin in 2 ml of 0.1N KOH. Water up to 100 ml.
2,4-D Stock-1 µmole/ml
To prepare 100 ml of 2,4-D stock solution.

| | |
|---|---|
| 2,4-D | 22.1 mg |
| Ethanol | 70% |

Dissolve 2,4-D in 2 ml of 70% ethanol, add water up to 100 ml.
NAA Stock Solution
To prepare 100 ml of stock NAA solution:

| | |
|---|---|
| NAA | 20 mg |
| Ethanol | 5 ml |

Add water to 100 ml.
Douglas Fir and Loblolly Pine Media for Subculture of Shoots
To prepare 500 ml of media:

| | | | |
|---|---|---|---|
| PBMO | 50% Stock | 10 | ml |
| Halide | 50% Stock | 10 | ml |
| Nitrate | 50% Stock | 10 | ml |
| Sulfate | 50% Stock | 10 | ml |
| Myo-inositol | | 0.10 | g |
| FeEDTA | 100% Stock | 5.0 | ml |
| Vitamins | 1000% Stock | 0.5 | ml |
| Sucrose | | 2.0% | |
| Agar | | 0.6% | |
| BAP | 0.2 mg/ml stock | 0.25 | ml |
| NAA | 0.1 mg/ml stock | 0.10 | ml |
| pH 5.8—5.9 | | | |

Add water up to 500 ml.
Adjust pH before autoclaving. Subculture every 5 to 6 weeks.
BO4 Media Modified BMH Medium For Expression of Picea Abies Embryos
Supplements to the BMH medium:

| | |
|---|---|
| Arginine | 40 mg |
| Asparagine | 100 mg |

Water up to 1000 ml. The modification also includes a change in eh macro salt to contain only 0.5% $KNO_3$.
Nutrient Medium (DMH) For Rescued Embryonal-Suspensor Masses of Douglas-Fir
To prepare 1000 ml of media:

| | |
|---|---|
| Nitrates | |
| $NH_4NO_3$ | 220 mg |
| $Ca(NO_3)_2.4H_2O$ | 278 mg |
| $KNO_3$ | 170 mg |
| Sulfates | |
| $MgSO_4.7H_2O$ | 185 mg |
| $MnSO_4.H_2O$ | 11.2 mg |
| $ZnSO_4.7H_2O$ | 4.3 mg |
| $CuSO_45H_2O$ | 0.013 mg |
| Halides | |
| $CaCl.2H_2O$ | 55 g |
| KI | 0.41 mg |
| $CoCl_2.6H_2O$ | 0.012 mg |
| NiCl | 0.012 mg |
| Phosphate, Borate, Molybdenate | |
| $KH_2PO_4$ | 85 mg |
| $H_3BO_3$ | 3.1 mg |
| $NaMoO_4$ | 0.12 mg |
| Fe.EDTA | |
| $FeSO_4.7H_2O$ | 13.96 mg |
| $Na_2EDTA.2H_2O$ | 18.62 mg |
| Vitamins | |
| Thiamine.HCl | 1.00 mg |
| Nicotinic acid | 0.5 mg |
| Pyridoxine.HCl | 0.50 mg |
| Carbon and Nitrogen Sources | |
| Sucrose | 30,000 mg |
| myo-inositol | 1,000 mg |
| Casein hydrolysate | 500 mg |
| L-glutamine | 450 mg |
| Glycine | 2 mg |
| L-tryptophan* | 1 mg |

*Tryptophan is added optionally if required.

Nutrient medium (DMH) for the culture of rescued embryonal-suspensor masses of Douglas fir is formulated in g/l and adjusted to pH 5.8 before autoclaving.

FeEDTA 100% stock
    To prepare 1 liter of 100% FeEDTA stock:

| | |
|---|---|
| FeSO$_4$—7H$_2$O | 2.780 g |
| Na$_2$EDTA—2H$_2$O | 3.723 g |

Heat (but do not boil) for about 1 to 2 hours. Not to be stored for more than a month.
Vitamin Stock 1000% stock
    To prepare 100 ml of 1000% vitamin stock:

| | |
|---|---|
| Thiamine-HCl | 0.10 g |
| Nicotine Acid | 0.05 g |
| Pyridoxine-HCl | 0.05 g |
| Glycine | 0.20 g |

LP Medium Stock (10×)
    To prepare 1 liter LP medium stock:

| | |
|---|---|
| NH$_4$NO$_3$ | 16.5 g |
| KNO$_3$ | 19.0 g |
| MgSO$_4$—7H$_2$O | 18.5 g |
| KH$_2$PO$_4$ | 3.4 g |
| CaCl—2H$_2$O | 0.22 g |
| H$_3$BO$_3$ | 0.31 g |
| MnSO$_4$ | 0.21 g |
| ZnSo$_4$ | 0.43 g |
| Na$_2$MoO$_4$ | 0.0125 g |
| CuSO$_4$—H$_2$O | 0.005 g |
| CoCl$_2$—H$_2$O | 0.00125 g |
| KI | 0.0415 g |
| FeEDTA Stock | 5.0 ml/l |
| Vitamin Stock | 1.0 ml/l |
| Water up to | 1000 ml |

These solutions represent the preferred general media used and concentrations of promotory growth regulators. The exact best acting media and growth regulators concentrations are species specific. The concentrations of growth regulators may be varied within limits so long as somatic polyembryogenesis is maintained. For example, certain auxins and cytokinins (promotory growth regulators may be substituted for each other (e.g., anilinopurine, or zeatin for BAP). Various amino acids may be used as a nitrogenous source.

EXAMPLE 2

Somatic Polyembryogenesis from Embryo Suspensor-mass of Sugar Pine (*Pinus lambertiana*) Embryos This example illustrates somatic polyembryogenesis from embryo suspensor-mass of sugar pine (Pinus Lambertiana) embryos.

Seeds from specific crosses in 1980 were provided by B. Kinlock, U.S. Forest Service, Berkeley, Calif. They were collected at the Institute of Forest Genetics, Placerville, Calif. and were maintained at 20° C. Seed coats were removed, surface-sterilized and the embryos excised aseptically before being placed on a range of modifications for two culture media described in *Physiol. Plant.*, 15:473–493 (1962).

Factors promoting embryogenesis were established using over 500 excised embryos through ten-fold replicated treatments under two different studies over a four month period. Growth stages and development of cells were followed by the light microscope and histologically according to the procedure described in *A. M. J. Bot.*, 55:123–142 (1968) and *Stain Technol.*, 51:179–185 (1976).

Excised embryos developed callus in all media within, four to five weeks. By ten to twelve weeks in mature five-year old seeds and three-four weeks in immature seeds ar unusually white mucilaginous mass was obtained from explants around the radicle on a variation of the DCR basal medium as described in Example 1. In this variation, the DCR basal medium contained 30, 50 and 500 mg of 2,4-dichlorophenoxyacetic acid (2,4-D), L-glutamine and casein hydrolysate, respectively. The clear mucilage surrounding the white embryonal-suspensor mass retained at 23° C. the same mOsmolality of the medium (ca., 125 mOsm). The mucilaginous embryonal-suspensor mass was found in only four-five percent of the total 200 embryos cultured under these conditions.

Microscopic examination of the embryonal-suspensor mass revealed globular embryos at various states of development with large suspensors protruding from the embryonal-suspensor mass. Cross-sections revealed that the somatic embryos contained shoot and root apices. Cells at the embryonal end were densely cytoplasmic with large nuclei staining. Development time and morphology were much like early stages of zygotic embryogenesis in conifers. Free nuclear stages were observed.

The embryogenic embryonal-suspensor mass has been maintained indefinitely so far on a 2,4-D supplemented medium. However, the development of the globular somatic embryos did not proceed beyond twelve weeks unless they were transferred to a medium lacking 2,4-D and containing 0.1 mg 1/l N$^6$-benzyladenine (BAP). Transfer of embryos encouraged elongation of the embryonic axis and the trueto-type development of six-eight cotyledons in all cases.

The embryogenic-suspensor mass originated from suspensor cells which remained attached to the radicle of the zygotic embryos. Embryos induced in the embryonal-suspensor mass of suspensor cells stained bright red with 0.10% (w/v) acetocarmine. When unstained callus and embryonal-suspensor mass were viewed under UV light, embryonic cells exhibited a characteristic green fluorescence. Moribund cells gave a bright yellow fluorescence. Suspensor cells revealed a weak fluorescence. This display permitted differentiation of the callus and embryonal-suspensor mass. The acetocarmine staining and fluorescence of cells has revealed that numerous embryonic cells are present initially in the mucilaginous matrix of elongated suspensor cells.

True-to-type developmental stages of embryogenesis were recapitulated within six weeks of culturing suspensor cells from immature seeds. The temporal processional stages of development occurred on the DCR basal medium supplemented with casein hydrolysate (500 mg 1/l) L-glutamine (200 mg 1/l), beta-indoleacetic acid (IAA) (0.2 mg 1/l), kinetin (0.1 mg 1/l) and myo-inositol (500 mg 1/l) at pH 5.9 (23° C.).

Transfer of embryos to a filter paper support in liquid medium lacking growth regulators promoted embryo elongation and the greening of cotyledons over 30 days. At this stage, the embryos were transferred to a basal medium without supplements and with 0.25% (w/v) activated charcoal under continuous light (2.8, 2.0, 0.5 $\mu$W cm$^2$ nm$^{-1}$) in the blue, red, and far-red range.

Embryos transferred to the basal medium without supplements and with activated charcoal under continuous light produced complete sugar pine plantlets within forty days at a low (one-two percent) conversion in the blue, red and far-red range.

EXAMPLE 3

Somatic Embryogenesis and Plantlet Regeneration from Norway Spruce (Picea Abies) Embryos This example illustrates somatic embryogenesis and plantlet regeneration from Norway Spruce (Picea Abies) embryos.

Seeds were collected (DDR Thuringeerwald Streufdorf, Lot No. 4-1347B and were provided by Dr. Peter Krogstrup), they were stored for two years at 4° C. Individual sees were surface sterilized and imbibed for twenty-four hours in sterile water. Embryos were excised and inoculated directly onto a basal culture medium (BM-2). A MS basal medium comprised of salts, vitamins and glycine with modified levels of $NH_4NO_3$ (550 mg/l), $KNO_3$ (4676 mg/l) and thiamine.HCl (0.1 mg/l) was formulated for somatic embryogenesis.

For induction of embryogenesis, half-strength modified-MS, basal medium was supplemented with casein hydrolysate (500 mg/l) myo-inositol (1000 mg/l), glutamine (450 mg/l) and sucrose (3%). This modification is identified as BM-1 other BM modifications are:

BM-2: BM-1+KN, BAP each $(20\times10^{-6}M)+2,4$-D $(50\times10^{-6}M)$.

BM-3: BM-1+KN, BAP each $(2\times10^{-6}M)+2,4$-D $(5\times10^{-6}M)$.

BM-4: BM-1+KN, BAP each $(2\times10^{-6}M)+2,4$-D $(1\times10^{-6}M)$.

All media were adjusted to pH 5.7 at 24° C. with KOH and HCl and solidified with Bacto-agar (Difco) 0.6%.

Test-tubes containing liquid medium were provided with filter paper support for explant, callus and embryonal-suspensor masses. All media with growth regulator were autoclaved at 1.1 kg $cm^{-2}$ at 121° C. for 20 minutes. Cultures were incubated in darkness at 23±1° C. at about 60% relative humidity, and transferred to light after thirty days for late embryogenic development.

All experiments demonstrating the somatic polyembryogenesis process were carried out with five replications and these replications were repeated at least three times.

Within thirty days on BM-2, 5–6% of the excised embryos developed two types of visually distinct callus. Callus developing from the cotyledons was green and compact. Callus from the radicals was white, translucent and embedded in a viscus mucilaginous matrix. This callus contained a proliferating embryonal-suspensor mass and was therefore not a callus in the true sense.

The non-embryogenic callus and proliferating embryonal-suspense masses were subcultured with low cytokinin and 2,4-D (BM-3). Within ten-fifteen days, numerous somatic embryos emerged from the white mucilaginous embryonal-suspensor mass derived from the radical. Embryos in this mass developed in networks of polyembryonic clusters. Each embryo consisted of a linear array of elongated cells at one end (like suspensors) and a small highly dense cluster of cells with large nuclei typical of developing embryos at the other end.

Embryogenic cell masses were maintained at several (about ten-twelve) day intervals by subculture on the same medium. Embryonic growth beyond the globular stage was always arrested in this BM-3 medium. For this reason, proliferating embryonal-suspensor masses with their polyembryonic clusters were transferred to a low concentration of 2,4-D $(1\times10^{-6})$ medium (BM-4). Within fifteen days, enlarged globular stages of development were observed. By fourteen days, approximately >25% of these numerous globular structures produced chlorophyll even when maintained in darkness. Morphogenesis of embryos continued on the same medium up to the torpedo stage of late embryonic development.

When the somatic embryos were transferred to a liquid medium without growth hormones (BM-1), globular embryos developed cotyledons and primary needles within thirty days in continuous light (2.8, 2.0 and 0.5 $\mu W$ $cm^{-2}$ $nm^{-1}$ in the blue, red and far-red).

Within twenty-five to thirty days, embryos developed into complete plantlets when transferred to basal medium (BM-1) with 0.25% (w/v) activated charcoal and without organic nitrogen (CH and gln). These plantlets were then established in soil.

Encapsulated embryos developed slightly and produced more chlorophyll when transferred to light. Histological studies showed that the somatic embryos with a root and shoot primordium remained organized during encapsulation. Viability of the encapsulated embryos was not affected within the time frame of this study.

In addition, fifty subcultures over 1.5 years were carried out on BM-3 at ten-to-twelve day intervals without reduction of embryogenic potential. Approximately 40±10 somatic spruce embryos representing the phenotype of the new generation were recovered within 150 days for each embryonal suspensor mass (approximately 50 mg fresh weight). The yield of somatic embryos was improved about 100±10 with the use of ABA according to Example 5.

EXAMPLE 4

Somatic Polyembryogenesis and Plantlet Regeneration in Loblolly Pine (Pinus taeda L.)

This example illustrates somatic polyembryogenesis and. plantlet regeneration in Loblolly Pine (Pinus taeda L.).

Improved seed of loblolly pine Pinus taeda L. were collected in June 1985 and obtained as gifts of Weyerhaeuser's forest seed orchard (Lyons, Ga.). Seed cones were stored at 4° C. until used for this study. Seeds from cones were excised and surface sterilized. Female gametophytes with attached suspensors and proembryos were excised from seeds every week just after fertilization (June 10–15) until seeds reached full maturity (September 30).

Initially each week, tissues were inoculated on defined cultures MS basal media, as described in Example 7. Factors evoking SPE and associated with this medium were established from over 1000 explants using five-fold replicated treatments. The MS basal medium was modified with addition of $NH_4NO_3$ (550 mg/l), $KNO_3$ (4674 mg/l), and thiamine.HCl (1.0 mg/l) and diluted to half-strength. Half-strength modified MS medium was further supplemented with myo-inositol (1000 mg/l), sucrose (3%), L-glutamine (450 mg/l), casein hydrolysate (500 mg/l), 2,4-D $(5\times10^{-5}M)$, kinetin $(2\times10^{-5}M)$, and $N^6$-benzyladenine $(2\times10^{-5}M)$ at an initial pH of 5.7 before autoclaving. Cultures were maintained on 0.6% agar (Difco Bacto) plates in darkness at 23±2° C.

Repetitive conifer-type SPE was obtained as follows. Within three to four weeks after fertilization and after inoculation on half-strength modified MS medium with supplements containing 2,4-D $(5\times10^{-5}M)$, KN and BAP $(2\times10^{-5}M)$, a white mucilaginous cellular mass was obtained in darkness from around the female gametophytes of the seeds. This embryonal-suspensor mass (ESM) was similar to the ESM described for Sugar pine in Example 2 and for Norway Spruce in Example 3.

To complete early embryogeny, the proliferating embryonal-suspensor mass bearing the early stages of SPE was subcultured in the same half-strength medium as described above, except that 2,4-D was present in $5 \times 10^{-6}$M, and KN and BAP each were present at $2 \times 10^{-6}$M concentration. After three or four subculture repetitions, the globular stage of embryogenesis was fully evident.

For cell suspension culture, approximately 2 g in 50 mls embryonal-suspensor masses were placed in shaking (120 rpm) 250 ml Erlenmeyer flasks with fluted bases. The culture medium was half-strength MS containing 2,4-D ($5 \times 10^{-6}$M), KN and BAP (each $1 \times 10^{-6}$M). Cell suspensions formed rapidly in darkness when maintained and subcultured on the same medium every five to six days. Repeated subculture produced well-dispersed suspensions of single cells, aggregates of two to five cells and larger embryonal-suspensor masses. Packed cell volume was measured after centrifugation of cell suspension of each flask at 250×g for ten minutes.

Cells in suspension cultures, or in embryonal-suspensor mass or callus were stained. Samples of cells in packed-cell volume of 5–10 $\mu$l were suspended in liquid medium to which 2% acetocarmine (1:1; v/v) was added. Cultures were heated slightly for fifteen seconds, and filtered to remove excess stain. 0.5% Evan's blue (1:1 v/v) was added to an acetocarmine stained cell suspension which was washed with medium to remove excess of stain and filtered. After double-staining, cultures were resuspended in 100% glycerol to improve optical clarity of cells on slides for microscopic inspection and the distribution of dyes followed microphotographically. The process was repeated with Feulgen and Evan's blue.

Callus was discarded and ESM was propagated in cell suspension.

Embryos elongated and developed cotyledons within eighth to ten weeks at 25°±2° C. when transferred to a sterile-filtered medium MS-2 or DCR-2 with filter papers support without growth regulators and under continuous white light (5.0, 2.0, 0.5 $\mu$W cm$^{-2}$ nm$^{-1}$ in blue, red and far-red, respectively) and cultured repeatedly for 7 days.

Complete plants were developed in a half-strength basal medium containing 0.25% (w/v) activated charcoal (E. Merck), myo-inositol (100 mg/l) and sucrose (2%) from which casein hydrolysate and glutamine were removed. This subcultured sequence completed the recovery of plantlets from embryonal-suspensor mass on agar plates.

Early embryogeny was produced repeatedly over one year by subculture on agar every ten to twelve days on the half-strength modified MS medium with supplements and 2,4-D ($5 \times 10^{-5}$M) and KN and BAP (each $2 \times 10^{-5}$M). Further embryonic development through the globular, embryo, cotyledon, shoot and root primordia and plantlet stage was evoked by sequential subculturing. Longitudinal sections of elongated somatic embryos with multiple cotyledons revealed shoot and root apices. Within nine to ten weeks, complete plantlets developed. Plantlets were grown to plants in a mixture containing peat moss, vermiculite and perlite with a ratio of 1:2:1.

Mucilaginous embryonal-suspensor masses were found in 9%–10% of the total explants cultured. Light microscopic examination of the masses revealed proembryonic stages and early embryonic stages. This proliferating embryonal-suspensor mass was not a callus because of its origin, cellular composition and developmental potential.

TABLE 2

| | Nucleus Staining Acetocarmine | Evan's | Cytoplasm Staining Acetocarmine | Evan's |
|---|---|---|---|---|
| A. Embryonal-suspensor Mass* proembryonal cells | 5 | 0 | 3** | 0 |
| suspensors | 1 | 4 | 0 | 2 |
| callus | 2 | 2 | 1 | 2 |
| free-nuclear stage*** | 5 | 3–4 | 1 | 1 |
| B. Nonembryogenic callus | 2 | 2 | 0 | 2 |

All units are in microns.
*Callus is not observed in the explant of the original embryonal-suspensor mass
**Some transvacuolar strands show vigorous streaming of organelles
***Individual nuclei differ in their ability to accept stain Table 2 illustrates affinity of organelles of cells in suspension cultures of loblolly pine at the end of a 10-day subculture for stains in the double-staining test: 5 very strong; 4 strong; 3 moderate; 2 weak; 1 very weak; 0 nil.

As shown in Table 2, two extreme major types of nuclei in the embryonal-suspensor mass are easily distinguished by the double staining method. First, there are the large nuclei, having larger than $10\mu$ diameter. These are proembryonal cells that give rise to SPE. These nuclei stain intensively with acetocarmine and Feulgen. Strands in the cytoplasm show an affinity for acetocarmine and may represent proembryonal cytoplasmic fibers. Elongated cells from proembryonal-suspensor mass which have been subcultured in the half strength modified MS medium with supplements 2,4-D ($5 \times 10^{-6}$), KN and BAP (each at $2 \times 10^{-6}$M) exhibit noticeable acetocarmine-reactive protoplasmic strands and nuclei after the double staining procedure. Second, smaller nuclei which are associated with the formation of suspensors derived from proembryonal cells, react with Evan's blue to further differentiate the cell mass. Exclusion of Evan's blue determines the viability of cells. Less viable cells and nuclei permit more dye to enter. By contrast in cells of nonembryogenic callus, nuclei are difficult to stain and locate by the same double staining procedure.

The origin of the blue-staining nuclei was evident after freezing the ESM in liquid nitrogen (−196° C.) for 30 minutes. The thawed ESM was placed on a modified half-strength MS basal medium with 2,4-D ($5 \times 10^{-6}$M) and KN and BAP ($2 \times 10^{-6}$M) medium. Upon recovery of cells, nearly all. of the suspensor cells of the blue staining nuclei were killed to leave viable embryonal cells with large nuclei. After three weeks, these cells divided with the production of suspensor with nuclei having a typical affinity for Evan's blue. Several rooted plantlets were recovered from these revived embryonal cells.

The above somatic embryogenic developmental sequence was repeated to the globular stage with embryonal-suspensor mass derived cell suspensions cultured in the 0.5 strength MS with 2,4-D ($5 \times 10^{-6}$M), KN and BAP (each $2 \times 10^{-6}$M). Growth and development of homogeneous cell suspensions was encouraged by subculturing to growth regulator free medium. After thirty days, globular embryos (0.43±0.02 mm diameter) with suspensors (4.5±0.23 mm length) were recovered at a level of 1040±200 embryos per 100 ml of medium. In somatic and zygotic embryogenesis, while subsequent divisions lead to the formation of massive suspensors with blue and red staining nuclei, many cells (45±20%) in the ESM retained nuclei with dominant red-staining properties. The division of the later contributed to the efficiency of the conifer-type somatic polyembryogenesis. From 0 to 10 days, the osmolality of the medium increased from 190 to over 220 mOsm, as the pH at 23° C.±1° C. dropped from 5.7 to 4.6. At lower pH, the cells suspensions deteriorated rapidly.

Histological inspection of the suspension cultured embryos revealed shoot and root apical meristems. This contrasted sharply to the unorganized growth and histological patterns obtained from nonembryogenic callus and suspension culture under the same treatments. By coupling the double staining procedure with fluorescence microscopy the lignification of suspensors could be observed at the onset of late embryogeny. Results with ESM and cell suspensions with and without addition of 2,4-D indicated that 2,4-D is significant for the induction and maintenance of a proliferating ESM. After removal of 2,4-D, the addition of NAA ($0.5 \times 10^{-6}$M) improved the growth and, development of somatic embryos. White light (2.8, 2.0, 0.5 $\mu$W cm$^{-2}$ nm$^{-1}$ in blue, red and far-red spectrum, respectively) was inhibitory to the early stages of SPE but stimulated late embryogeny and plantlet formation.

Somatic embryos were dipped in 1% (w/v) sodium alginate coming from a separatory funnel. After exposure to alginate the coated embryos were dropped in a beaker containing 100 mM calcium nitrate and stirred for eight to ten minutes. Encapsulated embryos were then washed with sterile water to remove excess of calcium nitrate. Embryonal-suspensor masses were freeze-preserved and embryos recovered by the procedure described by Can. J. Four. Res., 14:750–753 (1984).

Somatic embryos with cotyledons were separated and encapsulated in an alginate gel, as described above. Over fifteen capsulated somatic embryos were stored in darkness at 4° C.±2° C. for four months. All encapsulated embryos returned to 20° C. produced chlorophyll upon transfer to light. Their survival rate was not affected. Healthy plantlets were obtained from these stored embryos which developed in soil into plants.

EXAMPLE 5

Somatic Polyembryogenesis in Douglas-fir (*Pseudotsuga menziesii*)

This example illustrates somatic polyembryogenesis in Douglas-fir (*Pseudotsuga menziesii*).

Genetically improved seed of Douglas-fir (*Pseudotsuga menziesii*) were collected in June 1985 and obtained as gifts of Weyerhaeuser's forest seed orchard. Seed cones were stored at 4° C. until used for this study. Seeds from cones were excised and surface sterilized.

Female gametophytes with attached suspensors and proembryos were excised from seeds every week just after fertilization (June 15) until seeds reached full maturity (September 15). Each week, tissues were inoculated on two cultured media as described in Example 1. Factors evoking SPE from over 500 explants were established using five-fold replicated treatments.

Modified MS basal medium containing $NH_4HO_3$ (550 mg/l), $KNO_3$ (4674 mg/l), and thiamine.HCl (1.0 mg/l) was used. MS-1 half-strength modified MS medium was supplemented with myo-inositol (1000 mg/l), sucrose (3%), L-glutamine (450 mg/l), casein hydrolysate (500 mg/l).

DCR-1 was half-strength DCR salts with full-strength vitamins and glycine supplemented with myo-inositol (1000 mg/l), sucrose (3%), casein hydrolysate (500 mg/l) and glutamine (450 mg/l).

The used medium was further supplemented with 2,4-D ($5 \times 10^5$M) and KN and BAP ($2 \times 10^{-5}$M each) at an initial pH of 5.7, before autoclaving. Media were filter-sterilized. Cultures were maintained in dark at 23° C.±2° C. for 3–4 weeks.

After three-four weeks, a white slimy proliferating embryonal suspensor mass (ESM) was obtained from 20–25%±culture embryos on BM$_1$, with 2,4-D (5 c $10^{-5}$M), KN, BAP each at ($2 \times 10^{-5}$M). At this stage, ESM was subcultured to DCR$_1$ with 2,4-D ($5 \times 10^{-6}$M) KN, BAP each at ($2 \times 10^{-6}$M). ESM consists of embryonal cells (smaller cells with large nuclei and dense cytoplasm) which stain red with acetocarmine and suspensor cells which stained blue with Evan's blue. Subcultures were done every ten to twelve days intervals.

The ESM is also maintained in suspension culture (5 ml packed cell value in 40 ml DCR$_1$ liquified medium with 2,4-D, KN and BAP, rotating at 40–50 rpm in dark). Suspension cultures were maintained by subculture at about every seven day intervals. After tree to four subcultures, the ESM was transferred to DCR$_1$ liquid medium with 2,4-D ($1 \times 10^{-6}$M) and KN BAP each ($0.2 \times 10^{-6}$M). Proembryos were developed after one or to two subcultures in this medium. At this stage the ESM was transferred to a DCR$_1$ liquid medium with ABA ($1.25 \times 10^{-6}$M) for tree to four subcultures at every seven day intervals. The addition of ABA inhibited the polyembryogenesis process and encouraged the separation of proembryos. At this stage, these separated somatic proembryos were transferred to DCR-1 medium without ABA and incubated in dif fuse light. After three to four weeks, globular embryos were developed. These globular embryos were elongated and developed root primordia and shoots with cotyledons within two to three weeks.

EXAMPLE 6

Affect of Abscisic Acid (ABA) on Somatic Embryogenesis

This example illustrates affect of abscisic acid (ABA) on somatic embryogenesis.

Materials and Methods

Embryonal-suspensor masses growing on suspension culture on 2,4-D ($5 \times 10^{-6}$M), and KN, BAP (each $2 \times 10^{-6}$M) (BM-3, as described in Example 2, without agar) were transferred to basal medium (BM-1 in Example 2) with ABA ($1 \times 10^{-6}$M) without 2,4-D, KN and BAP. This consisted of five ml packed cell volume in 40 ml medium in 250 ml Erlenmeyer flasks rotating on 50 rpm in the dark at approximately 22° C. Subcultures were carried out by removal of old medium and the addition of fresh basal medium with ABA at every seven day intervals.

Results

Polyembryogenesis was inhibited after four-five subcultures with ABA. ABA inhibited the polyembryogenesis and encouraged the complete development of individual somatic embryos. Inhibition was effective in arresting the activities in cycle 1 (see FIG. 1) and launching proembryo development in Cycle 2 (FIG. 1). After four-five subcultures, complete embryos started growing on basal medium after the removal of ABA. This was observed in *Picea abies*, *Pinus taeda* and Douglas fir.

EXAMPLE 7

Somatic Polyembryogenesis from Gametophytic Tissue of Sugar Pine

This example illustrates somatic polyembrogenesis from gametophytic tissue of sugar pine.

Seed cones were supplied by forest Genetic Institute, Placerville, Calif. Seeds were isolated from these cones (after five to six weeks of fertilization). Seeds; were surface sterilized by a method described (Plant Cell Rept. 1985) and gametophytic tissue therefrom was cultured on half-strength DCR based medium with BAP (20 µmole) and 2,4-D (1 µmole). After fifteen to twenty days, the developing tissue was transferred to half-strength S-1 basal medium with 2,4-D (50 µmole) and KN and BAP (20 µmole). After two to three subcultures on same medium, an ESM developed. The ESM was transferred to half-strength DCR medium 2,4-D (5 µmole) and KN and BAP (1 µmole). Somatic polyembryos were developed. These embryos were further developed on half-strength DCR medium without any growth regulators. These embryos were further develop cotyledons, root and shoot primordia. Diploid embryos may also be developed by treating with colchicine.

EXAMPLE 8

Somatic Polyembryogenesis from Gametophytic Tissue of Sugar Pine

This example illustrates somatic polyembryogenesis from gametophytic tissue of sugar pine.

Seed cones were supplied by forest Genetic Institute, Placerville, Calif. Seeds were isolated from these cones after five to six weeks of fertilization. Seeds were surface sterilized and gametophytic tissue therefrom was cultured on half-strength DCR basal medium with BAP (20µ mole) and 2,4-D (1µ mole). After fifteen to twenty days, the developing tissue was transferred to half-strength MS-1 basal medium with 2,4-D (50 µmole), KN and BAP (20µ mole) each. After two to three subcultures on the same medium an ESM developed. The ESM was transferred to half-strength DCR medium 2,4-D (5 µmole) and KN and BAP (1µ mole) at a weekly subculture rate. Somatic polyembryos were developed. These embryos were further developed on half-strength DCR medium without any growth regulators. These embryos, which are haploid embryos, developed cotyledons, root and shoot primordia. Diploid embryos were developed by treating with colchicine.

EXAMPLE 9

Somatic Polyembryogenesis in Embryogenic Cell Masses of Picea Abies (Norway Spruce) and Pinus Taeda (Loblolly Pine) After Regeneration from Liquid Nitrogen This example illustrates somatic polyembryogenesis in embryogenic cell masses of Picea Abies (Norway Spruce) and Pinus Taeda (Loblolly Pine) after regeneration from liquid nitrogen.

For establishment of an embryonal-suspensor mass, half-strength Murashige-Skoog basal medium (BM-1) consisting of salts, glycine, and vitamins was used with the following modifications: $NH_4NO_3$ (275 mg/l), $KNO_3$ (2338 mg/l) and thiamine.HCl (1.0 mg/l). This formulation was supplemented with myo-inositol (1000 mg/l), casein hydrolysate (500 mg/l) and L-glutamine (450 mg/l).

Embryonal-suspensor masses were initiated from mature *Picea abies* (PA) embryos and immature *Pinus taeda* (PT) embryos 4 to 5 weeks after fertilization, on BM-1 medium supplemented with 2,4-D ($50\times10^{-6}$M), KN and BAP each $20\times10^{-6}$M. Proliferating embryonal-suspensor masses of PA and PT were maintained by subculturing every 12 to 13 days on BM-1 medium with 2,4-D ($5\times10^{-6}$M), KN and BAP each ($2\times10^{-6}$M). Globular embryos of PA were developed on BM-1 medium, containing 2,4-D ($1\times10^{-6}$M), KN and BAP ($2\times10^{-6}$M). PT embryos were developed on BM-1, medium supplemented with α-napthalene acetic acid (NAA) ($0.5\times 10^{-6}$M), KN and BAP each $1\times10^{-6}$M. Somatic embryos for both PA and PT became elongated and developed cotyledons when cultured on BM-1 liquid medium without growth regulators using a filter paper support under white light. Complete plantlets (PA and PT) were regenerated on BM-1 liquid medium without the presence of growth regulators, casein hydrolysate or glutamine. Inositol was present in 100 mg/l.

Optionally, individual true-to-type embryos exhibiting cotyledons, hypocotyl and radicals turning green, red and white respectively were encapsulated in a gel of 0.1 sodium alginate with 100 mM Ca $(NO_3)_2$. Several hundred of the encapsulated embryos were stored at 4° C.±1.0° C. in darkness for two months.

Portions of embryonal-suspensor masses (PA and PT) were treated with cryoprotective solution before freezing. The cryoprotectant was added to about 70 mg of cell masses that had been subcultured for 10 days. Cell masses were placed in a 10 ml glass tube, kept on ice, and either dimethylsulfoxide (DMSO) alone was added as 2.5%, 5% and finally 10% solution (w/v), or mixtures of polyethylene glycol (carbowax 6000) (glucose and DMSO in concentrations 2.5%:2%:2.5%, respectively, followed by 5%:4%:5%, and finally with 10%:8%:10% (w/v) were added sequentially and gradually at 15 minute intervals. After 30 minutes contact with final concentration of cryoprotectant, excess liquid was removed. The drained embryonal-suspensor masses were placed either into a corner of an aluminum freezing envelope (2.5×2.5 cm) or into a 2 ml polypropylene screw-capped Nunc vial. The aluminum envelope was made of a double layer of 0.0015" aluminum foil. Envelopes were sealed by double folding of the edges to avoid leakage. Envelopes and vials were placed in a programmed freezing chamber (Cryo-ed, Mount Clemens, Mass.), and cooled at approximately 1° C. per minute to −30° C., then plunged into liquid nitrogen and held there for 10 minutes. Samples were thawed rapidly by swirling in a 45° C. water batch before direct transfer to modified MS subculture agar medium. The cultures were maintained at 23° C.±1° C. to support the cell masses growth.

Double-staining with 2% acetocarmine and 0.5% Evan's blue was used to distinguish viable embryogenic, suspensor and callus cells among product recovered from liquid nitrogen. Products and their staining properties were compared with embryogenic tissues which were not frozen.

Table 3, below, summarizes the survival and growth of embryogenic cells of PA and PT five weeks after thawing embryonal-suspensor masses from liquid nitrogen.

TABLE 3

Survival and Growth of Embryogenic Cell Masses After Thawing from Liquid Nitrogen

| | PEG/GLUCOSE/DMSO | | DMSO | |
|---|---|---|---|---|
| | Aluminum Envelopes | Polypropylene Vials | Aluminum Envelopes | Polypropylene Vials |
| PA | 40 ± 3.5 | 65 ± 6.0 | 25 ± 3.0 | 40 ± 3.1 |
| PT | 20 ± 2.3 | 50 ± 5.6 | 15 ± 1.7 | 35 ± 4.0 |

The recovery of viable cells is based on comparison with unfrozen cell masses taken as 100%.

Table 3 illustrates the viability of embryonic cell masses after long-term storage in liquid nitrogen.

Survival was higher when treated with a mixture of cryoprotectants PEG, Glucose and DMSO) than with DMSO alone.

Frozen and thawed embryonal cells did not grow between 0 to 35 days. By contrast in the same interval, unfrozen embryonal-suspensor masses, whether untreated or cryoprotectant-treated grew from about 70 mg to 200 to 250 mg fresh weight. After 35 days, however, somatic proembryos having an elongated vacuolated suspensor cell at the tip, with dense cytoplasm and large nuclei were observed in thawed cellular masses. Subcultures were carried out every 10 to 12 day intervals. The slower growth of frozen and thawed cells reverted to almost normal growth rates after the third subculture. The delay was observed for PA and PT.

Early stages of somatic polyembryogenesis in those frozen embryonal cells were seen two weeks after the second subculture even though growth in fresh weight was inhibited. At least 6 to 8 somatic embryos were regenerated per gm fresh weight of inoculum as compared to 12 to 13 somatic embryos from unfrozen cellular masses. Somatic embryos of PA and PT developed cotyledons, roots and shoots after four to five months.

EXAMPLE 12

Induction of Morphogenesis Including Somatic Embryogenesis in Explants in Contact with ESMs This example illustrates induction of Morphogenesis including somatic embryogenesis in explants in contact with ESMs.

Aseptic explants of whole ripe embryos, excised from seeds, and cotyledons taken from germinating seeds from Douglas-fir, loblolly pine, Norway spruce and a tropical pine *Pinus merkusii* (10–100 mg fresh weight each) were isolated and placed on top of 500 mg of ESM from either Douglas-fir, loblolly pine or Norway spruce in all combinations with the above explants with ESMs were prepared and tested. Explants and ESM were cocultivated in Petri dishes containing BM-1 DCR-1 medium. Controls were explants placed on BM-1 or DCR-1 without ESMs. All explants were topologically in close contact with the mucilage of ESMs but were not submerged.

Leaves were removed from Douglas-fir taken from a 60-year old tree and placed individually in contact with ESMs of Douglas-fir on DCR-1 medium.

Cocultivation was performed at 23° C.±2° C. in continuous light or darkness. After 6 to 8 weeks, in all embryonic and mature leaves explants of Douglas-fir somatic embryogenesis (SE) was induced in epidermal cells of protodermal origin. SE was detected by recovery of proembryos having the characteristic double-staining properties. Proembryos were induced in areas topologically distinct from surface in contact with ESMs.

Explants of foreign species on ESMs tended to form callus or adventitious buds or shoots after 6 to 8 weeks.

For loblolly pine and Norway spruce somatic embryogenesis was more difficult to follow because explants tested to callus more so than controls in response to contact with ESMs. However, few somatic embryos were found among callus cells. While the origin of the induced SE was more difficult to trace in these cases, it was clear that ESMs contained embryo growth factors that led to the proliferation of peridermal cells of explants in unusual ways. Cells became very elongated, much like suspensor cells, and separated from the epidermis so that growth was upright, at right angles, to the epidermis much like normal somatic embryos emerging from ESM on a solid support. None of the controls gave the above responses except for slight callus formation.

One-dimensional polyacrylamide gel electrophoresis of crude protein fractions of acetocarmine-reactive ESMs were compared to proteins from non-embryonic, non acetocarmine reactive, cell masses of the same origin. Results indicate that a set of proteins uniquely found in the ESMs were present.

Although the foregoing invention has been described in some detail by the way of illustration and example for the purposes of clarity and understanding, it should be recognized that changes and modifications may be practiced within the scope of the appended claims.

What is claimed is:

1. A method for generating coniferous plants comprising steps:

(a) removing seeds from coniferous cones after about one to seven weeks following the fertilization;

(b) sterilizing the seeds by treating them with a detergent and water;

(c) removing a seed coat and excising ovules containing female gametophyte with proembryo, embryo and suspensor;

(d) placing the female gametophyte into a modified Murashige-Skoog or DCR medium each comprising ammonium nitrate, potassium nitrite and thiamine, and incubating it for about five to six weeks or until an embryonal suspensor mass develops around the female gametophyte;

(e) incubating the embryonal suspensor mass in a plant banal medium additionally containing 2, 4-dichlorophenoxyacatic acid, kinetin and $N^6$-benzyladenine, for about three to four weeks or until the embryonal suspensor mass develops into somatic embryos having elongated cells at the suspenicr end and dense cytoplasmic cells with large nuclei at the embryonal end;

(f) incubating the somatic embryos of step (e) in the medium of step (e) additionally containing naphthalene-2-acetic acid and optionally abecisic acid until the somatic embryo of stop (e) develops into a globular embryo;

(g) transferring globular embryos of stop (f) into the basial medium of step (d) and incubating the embryos in continuous light for about seven to eight days or until the embryos elongate and develop aultiple cotyledons;

(h) effecting conversion of emryos of step (g) to plantlets by incubating embryos in the basal medium of step (d)

optionally containing sucrose, casein hydrolysate and inositol until plantlets develop from somatic embryos; and (i) transferring the plantlets into containers containing sterile peat mass, vermiculite and perlite and letting the plantlets grow into adult plant.

2. A somatic polyembryogenesis method for clonal propagation of conifers via conifer true-to-type embryogenesis by culturing of an explant from genus Pinus, Piceae or Pseudotsuga, said explant comprising at least the female gametophyte excised from an immature seed or zygotic embryo having attached suspensor mass, said method comprising steps:

(a) isolating tissue or cells for somatic polyembryogenesis from cones or seeds from conifers;

(b) initiating formation of an embryonal mass suspensor by culturing the tissue or calls on basal medium enriched with plant growth regulators in darkness, at a temperature from about 21° C. to about 25° C. for 3 to 8 weeks;

(c) rescuing the embryonal mass suspensor by culturing the embryonal mass suspensor on basal medium enriched with promotory growth regulators for 1 to 8 weeks in darkness at temperatures from about 21° to about 25° C. and diagnostically differentiating the embryonal suspensor mass from nonembryogeric tissue or cells by presence of acetocarmine staining in the embryonal suspensor mass;

(d) separating embryonal suspensor mass from nonembryogenic cells or tissue;

(e) inducing development of proembryo and embryo by proliferating the embryonal suspensor mass by subculturing embryonal suspensor mass on a modified basal medium in darkness every 5 to 12 days for about 3 to about 4 weeks;

(f) enhancing development of the proembryo into embryo by promoting cleavage of proembryonal cells on a modified basal medium containing a plant growth regulator selected from the group consisting of auxins, cytokinins, cyclitols and a mixture thereof;

(g) subculturing the developed embryo on a modified medium containing abscisic acid and a reduced concentration of plant regulators in darkness or in a weak diffused light for 1–8 weeks to inhibit further cleavage polyembryogenesis;

(h) subculturing the embryo on a modified basal medium in continuous light for about 7 to 8 weeks to obtain elongated somatic embryos;

(i) converting elongated somatic embryos into mature embryos by further culturing elongated embryos on a modified basal medium; and (j) recovering the mature embryo.

3. The method of claim 2 further comprising step (k) for conversion of the mature embryo of step (j) into a plantlet and a plant by planting the mature embryos into a soil and growing the embryo into the plantlet for about 5–6 weeks and replanting the plantlet and growing the plantlet in full light into the plant.

4. The method of claim 2 further comprising step (1) wherein the mature embryo is encapsulated or desiccated for long-term storage.

5. The method of claim 2 further comprising step (m) wherein the mature embryo is cryoprotected by adding said embryo to a cryoprotectant and storing a cryoprotectant/embryo mixture in liquid nitrogen in darkness.

6. The method of claim 4 wherein the encapsulated embryo is cryoprotected by adding said embryo to a cryoprotectant and storing a cryoprotectant/encapsulated embryo in liquid nitrogen in darkness.

7. The method of claim 2 wherein the tissue or cells are obtained from *Pinus lambertiana* (Sugar pine), *Pinus taeda* (Loblolly pine), *Aristata engelm* (Hickory pine), *Monterumae lambertiana* (Rough-Barked Mexican pine), *Monticola douglas* (Western White Pine), *Pinus insignis* (Monterey pine), *Pinus sitchensis* (Sitka spruce), *Pinus glauca* (White spruce), *Pinus engelmanni* (Engelman spruce), *Picea abies* (Norway spruce), *Abies concolor* (Colorado spruce), *Abies fraseri* (Balsam fir); *Pseudotsuga mensilsui* (Douglas fir), *Pseudotsuga japonica* (Japanese fir), *Pseudotsuga macrocurpa* (Big Cone spruce) or *Sequoia sempervirens*.

8. The method of claim 7, wherein in step (b) the cells or tissue are cultured on the modified basal medium MS-2 or DCR-2 each comprising 2,4-D, kinetin and $N^6$-benzyladenine.

9. The method of claim 8 wherein the modified basal medium comprises $15\times10^{-5}M$ of 2,4-D and $2\times10^{-5}M$ of kinetin and $N^6$-benzyladenine each.

10. The method of claim 8 wherein in step (c) the embryonal mass suspensor is cultured on the basal medium MS-1 or DCR-1 each comprising casein hydrolysate, L-glutamine, myo-inositol and sucrose and wherein the promotory growth regulators are 2,4-D, kinetin and $N^6$-benzyladenine.

11. The method of claim 10 wherein the basal medium MS-1 or DCR-1 each comprises $5\times10^{-6}M$ of 2,4-D, and $2\times10^{-6}M$ of kinetin and $N^6$-benzyladenine each and 1000 mg/l of myo-inositol.

12. The method of claim 10 wherein the diagnostic differentiation in step (c) utilizes double staining technique wherein the cultured cells or tissue are stained with acetocarmine or Feulgen stain followed with staining with Evan's blue and wherein the embryogenic cells are distinguished from nonembryogenic cells or tissue by red stained nucleus and cytoplasm present in the embryogenic cells and wherein in nonembryogenic tissue only nucleus is weakly stained with acetocarmine and the cytoplasm stains only blue.

13. The method of claim 12 wherein in step 2(d) the acetocarmine or Feulgen stained cells and tissue are separated from blue stained nonembryogenic tissue or cells.

14. The method of claim 12 wherein in step (e) the enriched basal medium MS-2 or DCR-2 each comprising 2,4-D, kinetin and $N^6$-benzyladenine is used to establish a cell suspension culture of embryonal mass suspensor, said culture being subcultured in a fresh medium.

15. The method of claim 14 wherein the medium comprises $15\times10^{-5}M$ 2,4-D and $1\times10^{-5}M$ of kinetin and $N^6$-benzyladenine each and wherein the cell suspension culture is subcultured every 7 days.

16. The method of claim 14 wherein in step (f) the modified basal medium is MS-3 or DCR-3 medium each comprising 2,4-D, kinetin and $N^6$-benzyladenine.

17. The method of claim 16 wherein the medium comprises $15\times10^{-6}M$ of 2,4-D and $2\times10^{-6}M$ of kinetin and $N^6$-benzyladenine each.

18. The method of claim 17 wherein in step (g) the modified medium is MS-4 or DCR-4 each comprising naphthalene-2-acetic acid, kinetin and $N^6$-benzyladenine.

19. The method of claim 18 wherein the medium comprises $1\times10^{-6}M$ naphthalene-2-acetic acid and $2\times10^{-5}M$ of kinetin and $N^6$-benzyladenine each and wherein the embryo is subcultured 3–4 times.

20. The method of claim 19 wherein the medium additionally comprises abscisic acid.

21. The method of claim 20 wherein the medium comprises 1–4 μM of abscisic acid.

22. The method of claim 18, wherein in step (h) the modified basal medium is MS-1 or DCR-1 medium each comprising casein hydrolysate, L-glutamine, myo-inositol and sucrose.

23. The method of claim 22 wherein myo-inositol is present in a concentration of 100 mg/l.

24. The method of claim 22 wherein the culture is incubated in the presence of white light in the blue, red and far-red spectrum.

25. The method of claim 24 wherein the light spectrum is 2.8, 2.0 and 0.5 μw $cm^{-2}nm^{-1}$.

26. The method of claim 24 wherein the incubation temperature is about 24° C.–25° C.

27. The method of claim 22 wherein in step (i) the modified basal medium is MS-1 or DCR-1 medium each lacking casein hydrolysate and glutamine and each containing activated charcoal, sucrose, inositol, abscisic acid and cyclitol, and culture occurs in diffuse white light for 7–8 weeks.

28. The method of claim 27 wherein the medium comprises 0.25 (w/v) of activated charcoal, 7% sucrose and 100 mg/l myo-inositol.

* * * * *